US012774302B2

(12) United States Patent
Sekita et al.

(10) Patent No.: US 12,774,302 B2
(45) Date of Patent: Oct. 27, 2026

(54) METHOD FOR LOADING AMINO ACID ON RESIN FOR SOLID-PHASE SYNTHESIS

(71) Applicant: Chugai Seiyaku Kabushiki Kaisha, Tokyo (JP)

(72) Inventors: Hiroko Sekita, Tokyo (JP); Shio Komiya, Tokyo (JP); Katsunori Dan, Tokyo (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 659 days.

(21) Appl. No.: 18/269,334

(22) PCT Filed: Dec. 28, 2021

(86) PCT No.: PCT/JP2021/048743

§ 371 (c)(1),
(2) Date: Jun. 23, 2023

(87) PCT Pub. No.: WO2022/145444

PCT Pub. Date: Jul. 7, 2022

(65) Prior Publication Data

US 2024/0067674 A1 Feb. 29, 2024

(30) Foreign Application Priority Data

Dec. 28, 2020 (JP) ................................ 2020-218595

(51) Int. Cl.
*C07K 1/04* (2006.01)

(52) U.S. Cl.
CPC .................................. *C07K 1/042* (2013.01)

(58) Field of Classification Search
CPC ....................................................... C07K 1/04
See application file for complete search history.

(56) References Cited

U.S. PATENT DOCUMENTS

| | | | |
|---|---|---|---|
| 5,977,302 A | 11/1999 | Palmer et al. | |
| 6,103,698 A | 8/2000 | Barlozzari et al. | |
| 2006/0252093 A1 | 11/2006 | Meldal et al. | |
| 2009/0292108 A1 | 11/2009 | Chen et al. | |
| 2013/0143815 A1 | 6/2013 | Andersen et al. | |
| 2014/0128572 A1 | 5/2014 | Monnaie et al. | |
| 2015/0080549 A1 | 3/2015 | Kariyuki et al. | |
| 2019/0326890 A1 | 10/2019 | Luzi | |
| 2020/0277327 A1* | 9/2020 | Nomura | C07K 1/04 |
| 2023/0096766 A1 | 3/2023 | Muraoka et al. | |

FOREIGN PATENT DOCUMENTS

| | | | |
|---|---|---|---|
| CN | 102643330 | A | 8/2012 |
| CN | 110885360 | A | 3/2020 |
| JP | 2013533264 | A | 8/2013 |
| JP | 2014517022 | A | 7/2014 |
| WO | WO2013100132 | A1 | 7/2013 |
| WO | WO2018115864 | A1 | 6/2018 |
| WO | WO2018225851 | A1 | 12/2018 |
| WO | WO2020122182 | A1 | 6/2020 |

OTHER PUBLICATIONS

Amblard, M., et al., "Methods and Protocols of Modern Solid Phase Peptide Synthesis," Mol Biotechnol., 33(3):239-254 (2006).

Blankemeyer-Menge, B., et al., "An Efficient Method for Anchoring Fmoc-Amino Acids to Hydroxyl-Functionalised Solid Supports," Tetrahedron Lett., 31(12):1701-1704 (1990).

Chan, W. C. and White, P. D., editors, "Basic procedures, Fmoc solid phase peptide synthesis: A Practical Approach," 41-76 (2000).

Chatterjee, J., et al., "N-Methylation of Peptides: A New Perspective in Medicinal Chemistry," Acc Chem Res., 41(10):1331-1342 (2008).

Chatterjee, J., et al., "N-Methylation of Peptides and Proteins: An Important Element for Modulating Biological Functions," Angew Chem Int Ed., 52:254-269 (2013).

García-Martín, F., et al., "Chlorotrityl Chloride (CTC) Resin as a Reusable Carboxyl Protecting Group [1])[2])," QSAR Comb Sci., 26(10):1027-1035 (2007).

Gracia, S. R., et al., "Synthesis of chemically modified bioactive peptides: recent advances, challenges and developments for medicinal chemistry," Future Med Chem., 1(7):1289-1310 (2009).

Huang, Y., et al., "RNA Display Methods for the Discovery of Bioactive Macrocycles," Chem Rev., 119:10360-10391 (2019).

Hughes, A. B., editor, "Amino Acids, Peptides and Proteins in Organic Chemistry: Building Blocks, Catalysis and Coupling Chemistry," Chapter 7, vol. 3 (2011).

Jad, Y. E., et al., "2-Methyltetrahydrofuran and cyclopentyl methyl ether for green solid-phase peptide synthesis," Amino Acids, 48:419-426 (2016).

(Continued)

*Primary Examiner* — Shane Fang

(74) *Attorney, Agent, or Firm* — Nixon & Vanderhye P.C.

(57) ABSTRACT

An object of the present invention is to provide a method for efficiently producing a peptide compound of high purity at a high yield. It was found that an amino acid can be efficiently loaded on a resin for solid-phase synthesis by bringing an amino acid solution containing a specific solvent into contact with a resin for solid-phase synthesis that has been swollen with a specific solvent, thereby solving such problem.

20 Claims, No Drawings

(56) References Cited

OTHER PUBLICATIONS

Jaradat, D. M. M., "Thirteen decades of peptide synthesis: key developments in solid phase peptide synthesis and amide bond formation utilized in peptide ligation," Amino Acids, 50:39-68 (2018).
Merrifield, R. B., "Solid Phase Peptide Synthesis. I. The Synthesis of a Tetrapeptide," J Am Chem Soc., 85:2149-2154 (1963).
Nozaki, S., "Delay of coupling caused by excess additives," J Pep Sci., 12(2):147-153 (2006).
"Solid Phase Peptide Synthesis," Bachem—Pioneering Partner for Peptides, pp. 1-56, May 2020.
Spengler, J., et al., "Use of an Internal Reference for the Quantitative HPLC-UV Analysis of Solid-Phase Reactions: A Case Study of 2-Chlorotrityl Chloride Resin," ACS Comb Sci., 15:229-234 (2013).
Subirós-Funosas, R., et al., "Use of Oxyma as pH Modulatory Agent to be Used in the Prevention of Base-Driven Side Reactions and Its Effect on 2-Chlorotrityl Chloride Resin," Biopolymers (Pept Sci.), 98(2):89-97 (2012).
Teixido, M., et al., "Solid-phase synthesis and characterization of N-methyl-rich peptides," J Peptide Res., 65(2):153-166 (2005).
Yang, Y., "Side Reactions in Peptide Synthesis," Chapter 6, 119-161 (2015).

* cited by examiner

METHOD FOR LOADING AMINO ACID ON RESIN FOR SOLID-PHASE SYNTHESIS

CROSS-REFERENCE TO RELATED APPLICATIONS

This application is a U.S. National Phase of PCT Application No. PCT/JP2021/048743, filed Dec. 28, 2021, which claims priority to Japanese Patent Application No. 2020-218595, filed Dec. 28, 2020, the entire contents of each of which are herein incorporated by reference.

TECHNICAL FIELD

The present invention relates to a method for loading a starting compound on a resin for solid-phase synthesis in the production of a peptide compound by the solid-phase synthesis method, and a method for producing a peptide compound using this method.

BACKGROUND ART

Peptides are molecules in which a large number of amino acids are linked together, and naturally occurring peptides (natural peptides) exhibit various physiological activities. For the study of the physiological activities of natural peptides, the possible ways to obtain them as preparations are isolation from nature and chemical synthesis. To obtain them on a gram scale, such as when using preparations for testing and research, isolating substances naturally occurring in trace amounts is an extremely inefficient method. On the other hand, chemical synthesis allows to synthesize a peptide of interest by sequentially binding amino acids to obtain the desired sequence, and is therefore a more attractive method than isolating it from nature. However, in addition to amino and carboxyl groups, there may be other functional groups in the amino acids which can cause unintended structural transformations by arbitrary chemical reactions, and it is thus essential to establish a synthesis method to efficiently obtain the peptide with the sequence of interest. In addition, when physiologically active peptides are applied to drugs, more advanced chemical synthesis techniques are essential from the viewpoint of the supply and quality of the compound. Advances in such chemical synthesis techniques, particularly solid-phase synthesis method, are thought to have greatly contributed to the elucidation of the physiological activities of peptides (Non Patent Literature 1).

In recent years, it has become known that non-natural peptides with artificially designed peptide structures, especially medium molecular weight compounds with molecular weights of about 500 to 2000, can act effectively against tough targets, such as protein-protein interaction inhibition. In addition, medium molecular weight compounds are receiving attention as novel modalities that can be active compounds (modulators) of target proteins, which had been considered unsuitable as targets for drug discovery, and research to artificially design peptide structures and search for non-natural peptides with desired functions has been actively conducted (Non Patent Literature 2).

For the purpose of developing peptides as medicaments, it has been found that cyclization of peptides and the use of non-natural amino acids as the amino acids contained in the peptides improve their metabolic stability and membrane permeability (Non Patent Literatures 3 and 4).

Among cyclic peptides containing non-natural amino acids, cyclic peptides containing N-substituted amino acids in particular are now known to have excellent metabolic stability and membrane permeability, and to have drug likeness (Patent Literature 1).

It has also been suggested that macrocyclic peptides containing non-natural amino acids may be useful as inhibitors of protein-protein interactions (Non Patent Literature 5), and the conditions for cyclic peptides containing non-natural amino acids to be drug-like molecules have been identified (Patent Literatures 2 and 3).

Peptide synthesis is achieved by repeating the steps of (i) activating the carboxyl group of an amino acid having a protective group on the amino group and an unprotected carboxyl group with a condensing agent or the like to obtain an active ester (activation step), (ii) allowing the amino acid to act on a peptide having an unprotected N-terminus to obtain a peptide elongated with the amino acid (elongation step), and (iii) removing the protective group from the N-terminus of the elongated peptide (deprotection step)

to link a plurality of amino acids by amide bonds and elongate to a desired sequence. More specific methods of peptide synthesis include the liquid-phase method and the solid-phase method (Non Patent Literature 5).

Of these, the solid-phase method uses a resin for solid-phase synthesis, in which a group of atoms serving as linkers are bound to a polymer resin. The solid-phase method includes:

(a) a step of loading a carboxyl group of an amino acid having a protected amino group, on a linker atom group contained in a resin for solid-phase synthesis (loading step);

(b) a step of removing the protective group for the N-terminus amino group for deprotection (deprotection step);

(c) a step of activating the carboxyl group of the amino acid to be elongated (activation step);

(d) a step of elongating the amino acid (elongation step);

(e) a step of repeating the steps (b) to (d) as many times as necessary until a peptide chain of the sequence of interest is obtained; and (f) a step of cleaving the peptide of interest from the resin for solid-phase synthesis (deresination step).

As the amino acid protected at the N-terminus used in the elongation step, mainly amino acids in which the N-terminus amino group is protected with a Fmoc or Boc group are widely used (Non Patent Literatures 6 and 7).

Resins for solid-phase synthesis are broadly classified by linker atom group, and resins for solid-phase synthesis containing linker atom groups containing trityl and benzyl groups are widely used. Specifically, typical examples of such resins include CTC resins, Wang resins, SASRIN resins, and Rink Amide resins. These resins have different linker atom groups, and the reaction conditions for the deresination step differ depending on the linker atom group. The deresination step is mainly carried out under acidic conditions, but CTC resins, which can be deresinated with weak acids, contain a trityl group in the linker atom group, through which the peptide residues are loaded on the resin. On the other hand, Wang resins, which require a strong acid for deresination, contain a benzyl group in the linker atom group, through which the peptide residues are loaded on the resin. Thus, the resin used for solid-phase synthesis can be selected according to the chemical properties of the peptide of interest (Non Patent Literature 8).

When producing peptides containing N-methylamino acids in the sequence, the condensation reaction is slow due to steric hindrance of the N-methyl group, and the reduction in the yield of the target product due to racemization of the α-position of the amino acid residues has been an issue. Many problems have been reported, such as, in particular, the fact that the amide bond between an N-methylamino acid residue and an adjacent amino acid residue is susceptible to cleavage under acidic conditions, and that the amino acid residues are prone to elimination reactions due to the formation of diketopiperazine, and it is widely recognized that the synthesis of peptides containing N-methylamino acids is more difficult than the synthesis of peptides derived solely from natural amino acids (Non Patent Literature 9).

It is known that aspartic acid derivatives can be loaded on resins for solid-phase synthesis (Patent Literature 4). On the other hand, it is known that non-natural amino acids, including aspartic acid derivatives, may degrade in solution (Non Patent Literature 10).

It is also known that amino acids with a carboxyl group on the side chain, such as aspartic acid and glutamic acid, are prone to amide transfer reactions in which the carboxyl group on the side chain is transferred to the nitrogen atom in the main chain amide bond in the peptide residue depending on the solvent used in the peptide production step (Non Patent Literatures 10 and 11).

Thus, when synthesizing peptides that are unstable under acidic conditions, CTC resins which can undergo a deresination reaction with weak acids are useful (Non Patent Literature 12).

On the other hand, in the solid-phase synthesis of peptides using CTC resins, peptides can be deresinated from the CTC resin under mild conditions, and problems of premature cleavage (also called premature peptide release or premature acidolytic cleavage), where the amino acids or peptides loaded on the CTC resin are accidentally released, have been reported (Non Patent Literature 13).

It is also known that the binding site of the CTC resin to non-natural amino acids is hydrolyzed in the presence of water, and the step of loading non-natural amino acids on the CTC resin requires a reaction under non-aqueous conditions (Non Patent Literature 14).

CITATION LIST

Patent Literature

[Patent Literature 1] International Publication No. WO 2013/100132
[Patent Literature 2] International Publication No. WO 2018/115864
[Patent Literature 3] International Publication No. WO 2020/122182
[Patent Literature 4] International Publication No. WO 2018/225851

Non Patent Literature

[Non Patent Literature 1] J. Am. Chem. Soc., 1963, 85, 2149-2154.
[Non Patent Literature 2] Future Med. Chem., 2009, 1, 1289-1310.
[Non Patent Literature 3] Acc. Chem. Res., 2008, 41, 1331-1342.
[Non Patent Literature 4] Angew. Chem. Int. Ed., 2013, 52, 254-269.
[Non Patent Literature 5] Chem. Rev., 2019, 119, 10360-10391.
[Non Patent Literature 6] Amino Acids, Peptides and Proteins in Organic Chemistry: Building Blocks, Catalysis and Coupling Chemistry, Volume 3, 2011
[Non Patent Literature 7] Amino Acids, 2018, 50, 39-68.
[Non Patent Literature 8] Solid phase peptide synthesis (published by Bachem) [searched on Nov. 6, 2020], internet<URL: https://www.bachem.com/fileadmin/user_upload/pdf/Catalogs_Brochures/Solid_Phase_Peptide_Synthesis.pdf>
[Non Patent Literature 9] J. Peptide Res., 2005, 65, 153-166.
[Non Patent Literature 10] Side reaction in peptide synthesis, Academic Press, 2015, chapter 6, 119-161.
[Non Patent Literature 11] Biopolymers 2012, 98, 89-97.
[Non Patent Literature 12] QSAR Comb. Sci., 2007, 26, 1027-1035.
[Non Patent Literature 13] ACS Comb. Sci., 2013, 15, 229-234.
[Non Patent Literature 14] Article in Molecular Biotechnology, 2006, 33, 239-254.

SUMMARY OF INVENTION

Technical Problem

An object of the present invention is to provide a method for efficiently producing a peptide compound of high purity at a high yield.

For solid-phase synthesis of peptides containing N-substituted amino acids that are unstable under acidic conditions, it is considered appropriate to perform it using resins that allow removal of peptides from the resin for solid-phase synthesis under mild reaction conditions, such as CTC resins. The step of loading non-natural amino acids on a resin for solid-phase synthesis, and the step of elongating a peptide chain by condensing non-natural amino acids on a resin for solid-phase synthesis loading peptides containing natural and/or non-natural amino acids are performed by bringing a solution containing non-natural amino acids into contact with the resin for solid-phase synthesis or the peptide linked to it.

For the preparation of a non-natural amino acid solution, in addition to simply dissolving the non-natural amino acids in a solvent, the non-natural amino acids may be dissolved in the solvent after undergoing an operation such as a deprotection reaction.

When the non-natural amino acids are simply dissolved in a solvent to prepare a solution, if the non-natural amino acids are hydrates or hygroscopic, water will be mixed into the amino acid solution. In this case, the linker atom groups contained in the resin for solid-phase synthesis will undergo hydrolysis, which will degrade the resin and reduce the ability of the resin for solid-phase synthesis to load amino acids.

Furthermore, when functional group transformation such as deprotection reactions are performed on non-natural amino acids, the non-natural amino acids are present in solution during the operations of post-treatment after functional group transformation operation, such as compound extraction, isolation, solvent distillation, or dehydration by azeotropy, and therefore degradation of the non-natural amino acids can occur. For example, if there is a step of leaving or heating the non-natural amino acids in solution in the synthesis step, byproducts may be generated, reducing the yield of the target product and complicating the purification step. For example, if handling non-natural amino acids with large amounts of solvent in industrial production, the non-natural amino acids will be handled in the solvent for a longer time in the post-treatment step such as solvent extraction and in the step of concentrating the solution to obtain the product. Therefore, in large scale synthesis, the degradation of non-natural amino acids can be more pronounced, depending on the time stored in solution, the duration of the concentration step, and the handling temperature. In particular, in industrial production, these operations take a long time due to the larger amounts of reagents and solvents handled, and therefore the non-natural amino acids are kept in solution for a longer time, which results in more pronounced degradation reactions. Specifically, in addition to the amino groups and carboxyl groups on the main chain of the amino acids, amino acids with reactive functional groups, more specifically, aspartic acid and glutamic acid with carboxyl groups on the side chain, serine and threonine with hydroxyl groups on the side chain, lysine, glutamine, and asparagine with free amino groups on the side chain, cysteine and methionine with nucleophilic sulfur atoms on the side chain, tryptophan, tyrosine, and histidine with free NH and OH groups on the side chain, as well as derivatives thereof, can undergo unintended functional group transformation due to storage in solution.

An object of the present invention is to provide a method for efficiently producing a peptide compound of high purity containing non-natural amino acid residues at a high yield by suppressing the decrease in the loading ratio of amino acids due to degradation of the resin for solid-phase synthesis and suppressing the degradation of amino acids in the step of loading the amino acids on the resin for solid-phase synthesis to efficiently load the amino acids on the resin for solid-phase synthesis.

Solution to Problem

The present inventors investigated to solve the above problems and as a result, found that when amino acids are handled in a specific solvent, their degradation is suppressed. Specifically, the solvent used for swelling the resin for solid-phase synthesis and the solvent used for the subsequent reaction of loading the amino acids on the resin for solid-phase synthesis were identified. Furthermore, the present inventors have found an operation for carrying out the reaction of loading the amino acids on the resin for solid-phase synthesis after transforming a functional group in the amino acid to another functional group, without distilling off the solvent used in the transformation of the functional group. In addition, the present inventors have found a drying method for the amino acid solution that can suppress hydrolysis at the binding site between the linker atom group contained in the resin for solid-phase synthesis and the amino acid, and that does not require a dehydration operation involving the distillation of the solvent. These methods make it possible to suppress the degradation of amino acids and to efficiently load amino acids on a resin for solid-phase synthesis, and thereby allow to obtain a peptide compound of high yield and purity more efficiently than with conventional methods.

The present invention encompasses the following in a specific non-limiting aspect.

[1] A method for producing a peptide compound comprising at least one N-substituted amino acid, a salt thereof, or a solvate thereof, the method comprising a step of bringing a resin for solid-phase synthesis swollen in a solvent comprising a first solvent into contact with (i) a solution comprising an amino acid and a second solvent, or (ii) a solution comprising an amino acid, a second solvent, and a third solvent, to obtain an amino acid loaded on the resin for solid-phase synthesis (Step 1), wherein the first solvent and the third solvent are each independently selected from halogenated solvents, and the second solvent is an ether solvent.

[2] A method for producing an amino acid loaded on a resin for solid-phase synthesis, the method comprising a step of bringing a resin for solid-phase synthesis swollen in a solvent comprising a first solvent into contact with (i) a solution comprising an amino acid and a second solvent, or (ii) a solution comprising an amino acid, a second solvent, and a third solvent, wherein the first solvent and the third solvent are each independently selected from halogenated solvents, and the second solvent is an ether solvent.

[3] The method according to [1] or [2], wherein the solution is a solution comprising an amino acid and a second solvent.

[4] The method according to [1] or [2], wherein the solution is a solution comprising an amino acid, a second solvent, and a third solvent.

[5] The method according to [1], [2], or [4], wherein the first solvent and the third solvent are the same solvent.

[6] The method according to any one of [1] to [5], wherein the first solvent is selected from the group consisting of DCM, DCE, chloroform, chlorobenzene, and carbon tetrachloride.

[7] The method according to any one of [1] to [6], wherein the second solvent is selected from the group consisting of MeTHF, MTBE, CPME, THF, IPE, DME, diethyl ether, and dioxane.

[8] The method according to any one of [1] to [2] and [4] to [7], wherein the third solvent is selected from the group consisting of DCM, DCE, chloroform, chlorobenzene, and carbon tetrachloride.

[9] The method according to any one of [1] to [2] and [4] to [8], wherein the volume ratio of the second solvent to the third solvent is 1:1 to 1:10.

[10] The method according to any one of [1] to [3] and [5] to [9], wherein the solution comprising an amino acid and a second solvent is a solution obtained by an extraction operation comprising the use of a second solvent, which is performed after the deprotection reaction of the protective group for the amino acid's carboxyl group prior to step 1, and a subsequent optional dehydration operation.

[11] The method according to any one of [1] to [2] and [4] to [9], wherein the solution comprising an amino acid, a second solvent, and a third solvent is a solution obtained by further adding a third solvent to a solution obtained by an extraction operation comprising the use of a second solvent, which is performed after the deprotection reaction of the protective group for the amino acid's carboxyl group prior to step 1, and a subsequent optional dehydration operation.

[12] The method according to [10] or [11], wherein the dehydration operation is performed with a desiccant.

[13] The method according to [12], wherein the desiccant is $Na_2SO_4$, $MgSO_4$, or $CaCl_2$).

[14] The method according to any one of [10] to [13], wherein the protective group for the carboxyl group can be removed with an acid.

[15] The method according to any one of [10] to [14], wherein the protective group for the carboxyl group is t-Bu, trityl, methoxytrityl, or cumyl.

[16] The method according to any one of [1] to [15], wherein the resin for solid-phase synthesis is a CTC resin, a Wang resin, a SASRIN resin, a Trt resin, an Mtt resin, or an Mmt resin.

[17] The method according to [16], wherein the resin for solid-phase synthesis is a CTC resin.

[18] The method according to any one of [1] to [17], wherein the amino acid is a non-natural amino acid.

[19] The method according to [18], wherein the non-natural amino acid is a non-natural N-substituted amino acid.

[20] The method according to [18] or [19], wherein the non-natural amino acid is loaded on the resin for solid-phase synthesis by a carboxyl group bound to the carbon atom at the β-position or the carbon atom at the γ-position of the amino group.

[21] The method according to any one of [18] to [20], wherein the non-natural amino acid comprises an aminocarbonyl group.

[22] The method according to [20] or [21], wherein the non-natural amino acid loaded on the resin for solid-phase synthesis by a carboxyl group bound to the carbon atom at the β-position or the carbon atom at the γ-position of the amino group is aminocarbonylated aspartic acid, aminocarbonylated glutamic acid, 2-aminobutanoic acid, or an N-substituted form thereof, and wherein the aminocarbonylated aspartic acid is aminocarbonylated at a free carboxyl group of aspartic acid and the aminocarbonylated glutamic acid is aminocarbonylated at a free carboxyl group of glutamic acid.

[23] The method according to any one of [1] and [3] to [22], wherein at least one N-substituted amino acid in the peptide compound is a non-natural N-substituted amino acid.

[24] The method according to any one of [1] and [3] to [23], wherein the peptide compound comprises two or more N-substituted amino acids.

[25] The method according to any one of [1] and [3] to [24], wherein 30% or more of the total number of amino acids constituting the peptide compound are N-substituted amino acids.

[26] A method for producing a cyclic peptide compound, a salt thereof, or a solvate thereof, comprising the following steps:

a step of obtaining a peptide compound comprising at least one N-substituted amino acid, a salt thereof, or a solvate thereof, according to the method according to any one of [1] and [3] to [25], a step of removing the resin for solid-phase synthesis, and a step of cyclizing the C-terminus group and the N-terminus group of the peptide compound, the salt thereof, or the solvate thereof to form a cyclic portion.

Advantageous Effect of Invention

According to the present invention, which uses a specific solvent when swelling the resin for solid-phase synthesis and when loading amino acids on the resin for solid-phase synthesis, amino acids can be loaded on the resin for solid-phase synthesis at a high loading ratio and high yield. In the present invention, since the amino acid solution used in the reaction to load amino acids on the resin can be prepared without undergoing concentration or heating, the time that amino acids are stored in solution can be shortened, amino acid degradation can be suppressed, and a high percentage of amino acids can be loaded on the resin for solid-phase synthesis. Moreover, in the present invention, by applying specific operations, including the use of the solvents used in the loading step and desiccants, to the post-treatment of the deprotection step preceding the loading step, the amino acid solution used in the loading step can be obtained without isolating or purifying the deprotected amino acids, and a high percentage of amino acids can be loaded on the resin for solid-phase synthesis. In addition, in the present invention, no operations such as azeotropic dehydration or heated drying are performed prior to the preparation of the amino acid solution, and therefore the amino acids are not stored in solution for a long time and can be efficiently loaded on the resin even in industrial-scale synthesis. The present invention is applicable to the production of a peptide compound containing any type and number of amino acids and can be a useful method for producing a peptide compound in a high yield and high purity.

DESCRIPTION OF EMBODIMENTS

Abbreviations

The abbreviations used in the present invention are listed below.

Asp: aspartic acid
CTC Resin: 2-chlorotrityl chloride resin
CPME: cyclopentyl methyl ether
DCE: 1,2-dichloroethane
DCM: dichloromethane
DIPEA: diisopropylethylamine
DME: 1,2-dimethoxyethane
DMF: N,N-dimethylformamide
Fmoc: 9-fluorenylmethyloxycarbonyl group
HMDS: hexamethyldisilazane
IPE: diisopropyl ether
Me: methyl group
MeAsp: N-methyl aspartic acid
MeTHF: 2-methyltetrahydrofuran
MTBE: t-butyl methyl ether
pip: piperidinyl group
pyrro: pyrrolidinyl group
TFA: trifluoroacetic acid
THF: tetrahydrofuran
TMSOTf: trimethylsilyl trifluoromethanesulfonate (Definition of Functional Group and the Like)

In the present specification, examples of the "halogen atom" include F, Cl, Br and I.

In the present specification, the "alkyl" is a monovalent group induced by the removal of one arbitrary hydrogen atom from aliphatic hydrocarbon, and has a subset of a hydrocarbyl or hydrocarbon group structure containing hydrogen and carbon atoms without containing a heteroatom (which refers to an atom other than carbon and hydrogen atoms) or an unsaturated carbon-carbon bond in the skeleton. The alkyl includes not only a linear form but a branched form. The alkyl is specifically alkyl having 1 to 20 carbon atoms ($C_1$-$C_{20}$; hereinafter, "$C_p$-$C_q$" means that the number of carbon atoms is p to q), preferably $C_1$-$C_{10}$ alkyl, more preferably $C_1$-$C_6$ alkyl. Examples of the alkyl specifically include methyl, ethyl, n-propyl, i-propyl, n-butyl, s-butyl, t-butyl, isobutyl (2-methylpropyl), n-pentyl, s-pentyl (1-methylbutyl), t-pentyl (1,1-dimethylpropyl), neopentyl (2,2-dimethylpropyl), isopentyl (3-methylbutyl), 3-pentyl (1-ethylpropyl), 1,2-dimethylpropyl, 2-methylbutyl, n-hexyl, 1,1,2-trimethylpropyl, 1,2,2-trimethylpropyl, 1,1,2,2-tetramethylpropyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, and 2-ethylbutyl.

In the present specification, the "alkenyl" is a monovalent group having at least one double bond (two adjacent $SP^2$ carbon atoms). Depending on the conformation of the double bond and a substituent (if present), the geometric morphology of the double bond can assume entgegen (E) or zusammen (Z) and cis or trans conformations. The alkenyl includes not only a linear form but a branched form. The alkenyl is preferably $C_2$-$C_{10}$ alkenyl, more preferably $C_2$-$C_6$ alkenyl. Examples thereof specifically include vinyl, allyl, 1-propenyl, 2-propenyl, 1-butenyl, 2-butenyl (which includes cis and trans), 3-butenyl, pentenyl, 3-methyl-2-butenyl, and hexenyl.

In the present specification, the "alkynyl" is a monovalent group having at least one triple bond (two adjacent SP carbon atoms). The alkynyl includes not only a linear form but a branched form. The alkynyl is preferably $C_2$-$C_{10}$ alkynyl, more preferably $C_2$-$C_6$ alkynyl. Examples thereof specifically include ethynyl, 1-propynyl, propargyl, 3-butynyl, pentynyl, hexynyl, 3-phenyl-2-propynyl, 3-(2'-fluorophenyl)-2-propynyl, 2-hydroxy-2-propynyl, 3-(3-fluorophenyl)-2-propynyl, and 3-methyl-(5-phenyl)-4-pentynyl.

In the present specification, the "cycloalkyl" means a saturated or partially saturated cyclic monovalent aliphatic hydrocarbon group and includes a monocyclic ring, a bicyclo ring, and a spiro ring. The cycloalkyl is preferably $C_3$-$C_8$ cycloalkyl. Examples thereof specifically include cyclopropyl, cyclobutyl, cyclopentyl, cyclohexyl, cycloheptyl, cyclooctyl, bicyclo[2.2.1]heptyl, and spiro[3.3]heptyl.

In the present specification, the "aryl" means a monovalent aromatic hydrocarbon ring and is preferably $C_6$-$C_{10}$ aryl. Examples of the aryl specifically include phenyl and naphthyl (e.g., 1-naphthyl and 2-naphthyl).

In the present specification, the "heterocyclyl" means a nonaromatic cyclic monovalent group containing a carbon atom as well as 1 to 5 heteroatoms. The heterocyclyl may have a double and/or triple bond in the ring. A carbon atom in the ring may form carbonyl through oxidation, and the ring may be a monocyclic ring or a condensed ring. The number of atoms constituting the ring is preferably 4 to 10 (4- to 10-membered heterocyclyl), more preferably 4 to 7 (4- to 7-membered heterocyclyl). Examples of the heterocyclyl specifically include azetidinyl, oxiranyl, oxetanyl, azetidinyl, dihydrofuryl, tetrahydrofuryl, dihydropyranyl, tetrahydropyranyl, tetrahydropyridyl, tetrahydropyrimidyl, morpholinyl, thiomorpholinyl, pyrrolidinyl, piperidinyl, piperazinyl, pyrazolidinyl, imidazolinyl, imidazolidinyl, oxazolidinyl, isoxazolidinyl, thiazolidinyl, isothiazolidinyl, 1,2-thiazinane, thiadiazolidinyl, azetidinyl, oxazolidone, benzodioxanyl, benzoxazolyl, dioxolanyl, dioxanyl, tetrahydropyrrolo[1,2-c]imidazole, thietanyl, 3,6-diazabicyclo[3.1.1]heptanyl, 2,5-diazabicyclo[2.2.1]heptanyl, 3-oxa-8-azabicyclo[3.2.1]octanyl, sultam, and 2-oxaspiro[3.3]heptyl.

In the present specification, the "protected heterocyclyl" means a group in which one or more functional groups, for example, an amino group, contained in the "heterocyclyl" defined above, is protected with an arbitrary protective group, and is preferably protected 4- to 7-membered heterocyclyl. Examples of the protective group specifically include Boc, Fmoc, Cbz, Troc, and Alloc. Examples of the protected heterocyclyl specifically include Boc-protected azetidine.

In the present specification, the "heterocycloalkylidene" means a divalent group that results from the removal of two hydrogen atoms from one carbon atom of the "heterocyclyl" defined above and has a free valence that constitutes a portion of a double bond. The heterocycloalkylidene is preferably 4- to 7-membered heterocycloalkylidene. Examples thereof specifically include tetrahydropyran-4-ylidene and azetidin-3-ylidene.

In the present specification, the "protected heterocycloalkylidene" means a group in which one or more functional groups, for example, an amino group, contained in the "heterocycloalkylidene" defined above, is protected with an arbitrary protective group, and is preferably protected 4- to 7-membered heterocycloalkylidene. Examples of the protective group specifically include Boc, Fmoc, Cbz, Troc, and Alloc. Examples of the protected heterocyclyl specifically include Boc-protected azetidin-3-ylidene.

In the present specification, the "heteroaryl" means an aromatic cyclic monovalent group containing a carbon atom as well as 1 to 5 heteroatoms. The ring may be a monocyclic ring or a condensed ring with another ring and may be partially saturated. The number of atoms constituting the ring is preferably 5 to 10 (5- to 10-membered heteroaryl), more preferably 5 to 7 (5- to 7-membered heteroaryl). Examples of the heteroaryl specifically include furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyrimidyl, pyridazinyl, pyrazinyl, triazinyl, benzofuranyl, benzothienyl, benzothiadiazolyl, benzothiazolyl, benzoxazolyl, benzoxadiazolyl, benzimidazolyl, indolyl, isoindolyl, indazolyl, quinolyl, isoquinolyl, cinnolinyl, quinazolinyl, quinoxalinyl, benzodioxolyl, indolizinyl, and imidazopyridyl.

In the present specification, the "alkoxy" means an oxy group bonded to the "alkyl" defined above and is preferably $C_1$-$C_6$ alkoxy. Examples of the alkoxy specifically include methoxy, ethoxy, 1-propoxy, 2-propoxy, n-butoxy, i-butoxy, s-butoxy, t-butoxy, pentyloxy, and 3-methylbutoxy.

In the present specification, the "alkenyloxy" means an oxy group bonded to the "alkenyl" defined above and is preferably $C_2$ to $C_6$ alkenyloxy. Examples of the alkenyloxy specifically include vinyloxy, allyloxy, 1-propenyloxy, 2-propenyloxy, 1-butenyloxy, 2-butenyloxy (which includes cis and trans), 3-butenyloxy, pentenyloxy, and hexenyloxy.

In the present specification, the "cycloalkoxy" means an oxy group bonded to the "cycloalkyl" defined above and is preferably $C_3$-$C_8$ cycloalkoxy. Examples of the cycloalkoxy specifically include cyclopropoxy, cyclobutoxy, and cyclopentyloxy.

In the present specification, the "aryloxy" means an oxy group bonded to the "aryl" defined above and is preferably $C_6$-$C_{10}$ aryloxy. Examples of the aryloxy specifically include phenoxy, 1-naphthyloxy, and 2-naphthyloxy.

In the present specification, the "amino" means $—NH_2$ in the narrow sense and means —NRR' in the broad sense. In this context, R and R' are each independently selected from hydrogen, alkyl, alkenyl, alkynyl, cycloalkyl, heterocyclyl, aryl, and heteroaryl, or R and R' form a ring together with the nitrogen atom bonded thereto. Examples of the amino preferably include $—NH_2$, mono-$C_1$-$C_6$ alkylamino, di-$C_1$-$C_6$ alkylamino, and 4- to 8-membered cyclic amino.

In the present specification, the "monoalkylamino" means a group of the "amino" defined above in which R is hydrogen, and R' is the "alkyl" defined above, and is preferably mono-$C_1$-$C_6$ alkylamino. Examples of the mono-alkylamino specifically include methylamino, ethylamino, n-propylamino, i-propylamino, n-butylamino, s-butylamino, and t-butylamino.

In the present specification, the “dialkylamino” means a group of the “amino” defined above in which R and R' are each independently the “alkyl” defined above, and is preferably di-$C_1$-$C_6$ alkylamino. Examples of the dialkylamino specifically include dimethylamino and diethylamino.

In the present specification, the “cyclic amino” means a group of the “amino” defined above in which R and R' form a ring together with the nitrogen atom bonded thereto, and is preferably 4- to 8-membered cyclic amino. Examples of the cyclic amino specifically include 1-azetidyl, 1-pyrrolidyl, 1-piperidyl, 1-piperazyl, 4-morpholinyl, 3-oxazolidyl, 1,1-dioxidothiomorpholinyl-4-yl, and 3-oxa-8-azabicyclo[3.2.1]octane-8-yl.

In the present specification, the “protected amino” means an amino group protected with an arbitrary protective group. Examples of the protected amino specifically include amino protected with a protective group such as Boc, Fmoc, Cbz, Troc, or Alloc.

In the present specification, the “aminocarbonyl” means a carbonyl group bonded to the “amino” defined above and is preferably —$CONH_2$, mono-$C_1$-$C_6$ alkylaminocarbonyl, di-$C_1$-$C_6$ alkylaminocarbonyl, or 4- to 8-membered cyclic aminocarbonyl. Examples of the aminocarbonyl specifically include —$CONH_2$, dimethylaminocarbonyl, 1-azetidinylcarbonyl, 1-pyrrolidinylcarbonyl, 1-piperidinylcarbonyl, 1-piperazinylcarbonyl, 4-morpholinylcarbonyl, 3-oxazolidinylcarbonyl, 1,1-dioxidothiomorpholinyl-4-ylcarbonyl, and 3-oxa-8-azabicyclo[3.2.1]octane-8-ylcarbonyl.

In the present specification, the “alkenyloxycarbonyl” means a carbonyl group bonded to the “alkenyloxy” defined above and is preferably $C_2$-$C_6$ alkenyloxycarbonyl. Examples of the alkenyloxycarbonyl specifically include vinyloxycarbonyl, allyloxycarbonyl, 1-propenyloxycarbonyl, 2-propenyloxycarbonyl, 1-butenyloxycarbonyl, 2-butenyloxycarbonyl (which includes cis and trans), 3-butenyloxycarbonyl, pentenyloxycarbonyl, and hexenyloxycarbonyl.

In the present specification, the “alkylsulfonyl” means a sulfonyl group bonded to the “alkyl” defined above and is preferably $C_1$-$C_6$ alkylsulfonyl. Examples of the alkylsulfonyl specifically include methylsulfonyl.

In the present specification, the “hydroxyalkyl” means a group in which one or more hydrogen of the “alkyl” defined above are replaced with a hydroxy group, and is preferably $C_1$-$C_6$ hydroxyalkyl. Examples of the hydroxyalkyl specifically include hydroxymethyl, 1-hydroxyethyl, 2-hydroxyethyl, 2-hydroxy-2-methylpropyl, and 5-hydroxypentyl.

In the present specification, the “haloalkyl” means a group in which one or more hydrogen of the “alkyl” defined above are replaced with halogen, and is preferably $C_1$-$C_6$ haloalkyl, more preferably $C_1$-$C_6$ fluoroalkyl. Examples of the haloalkyl specifically include difluoromethyl, trifluoromethyl, 2,2-difluoroethyl, 2,2,2-trifluoroethyl, 3,3-difluoropropyl, 4,4-difluorobutyl, and 5,5-difluoropentyl.

In the present specification, the “cyanoalkyl” means a group in which one or more hydrogen of the “alkyl” defined above are replaced with cyano, and is preferably $C_1$-$C_6$ cyanoalkyl. Examples of the cyanoalkyl specifically include cyanomethyl and 2-cyanoethyl.

In the present specification, the “aminoalkyl” means a group in which one or more hydrogen of the “alkyl” defined above are replaced with the “amino” defined above, and is preferably $C_1$-$C_6$ aminoalkyl. Examples of the aminoalkyl specifically include 1-piperidylmethyl, 2-(1-piperidyl)ethyl, 3-(1-piperidyl)propyl, and 4-aminobutyl.

In the present specification, the “carboxyalkyl” means a group in which one or more hydrogen of the “alkyl” defined above are replaced with carboxy, and is preferably $C_2$-$C_6$ carboxyalkyl. Examples of the carboxyalkyl specifically include carboxymethyl.

In the present specification, the “alkenyloxycarbonylalkyl” means a group in which one or more hydrogen of the “alkyl” defined above are replaced with the “alkenyloxycarbonyl” defined above, and is preferably $C_2$-$C_6$ alkenyloxycarbonyl-$C_1$-$C_6$ alkyl, more preferably $C_2$-$C_6$ alkenyloxycarbonyl-$C_1$-$C_2$ alkyl. Examples of the alkenyloxycarbonylalkyl specifically include allyloxycarbonylmethyl and 2-(allyloxycarbonyl)ethyl.

In the present specification, the “alkoxyalkyl” means a group in which one or more hydrogen of the “alkyl” defined above are replaced with the “alkoxy” defined above, and is preferably $C_1$-$C_6$ alkoxy-$C_1$-$C_6$ alkyl, more preferably $C_1$-$C_6$ alkoxy-$C_1$-$C_2$ alkyl. Examples of the alkoxyalkyl specifically include methoxymethyl, ethoxymethyl, 1-propoxymethyl, 2-propoxymethyl, n-butoxymethyl, i-butoxymethyl, s-butoxymethyl, t-butoxymethyl, pentyloxymethyl, 3-methylbutoxymethyl, 1-methoxyethyl, 2-methoxyethyl, and 2-ethoxyethyl.

In the present specification, the “cycloalkylalkyl” means a group in which one or more hydrogen of the “alkyl” defined above are replaced with the “cycloalkyl” defined above, and is preferably $C_3$-$C_8$ cycloalkyl-$C_1$-$C_6$ alkyl, more preferably $C_3$-$C_6$ cycloalkyl-$C_1$-$C_2$ alkyl. Examples of the cycloalkylalkyl specifically include cyclopropylmethyl, cyclobutylmethyl, cyclopentylmethyl, and cyclohexylmethyl.

In the present specification, the “cycloalkoxyalkyl” means a group in which one or more hydrogen of the “alkyl” defined above are replaced with the “cycloalkoxy” defined above, and is preferably $C_3$-$C_8$ cycloalkoxy-$C_1$-$C_6$ alkyl, more preferably $C_3$-$C_6$ cycloalkoxy-$C_1$-$C_2$ alkyl. Examples of the cycloalkoxyalkyl specifically include cyclopropoxymethyl and cyclobutoxymethyl.

In the present specification, the “heterocyclylalkyl” means a group in which one or more hydrogen of the “alkyl” defined above are replaced with the “heterocyclyl” defined above, and is preferably 4- to 7-membered heterocyclyl-$C_1$-$C_6$ alkyl, more preferably 4- to 7-membered heterocyclyl-$C_1$-$C_2$ alkyl. Examples of the heterocyclylalkyl specifically include 2-(tetrahydro-2H-pyran-4-yl)ethyl and 2-(azetidin-3-yl)ethyl.

In the present specification, the “alkylsulfonylalkyl” means a group in which one or more hydrogen of the “alkyl” defined above are replaced with the “alkylsulfonyl” defined above, and is preferably $C_1$-$C_6$ alkylsulfonyl-$C_1$-$C_6$ alkyl, more preferably $C_1$-$C_6$ alkylsulfonyl-$C_1$-$C_2$ alkyl. Examples of the alkylsulfonylalkyl specifically include methylsulfonylmethyl and 2-(methylsulfonyl)ethyl.

In the present specification, the “aminocarbonylalkyl” means a group in which one or more hydrogen of the “alkyl” defined above are replaced with the “aminocarbonyl” defined above, and is preferably aminocarbonyl-$C_1$-$C_6$ alkyl, more preferably aminocarbonyl-$C_1$-$C_4$ alkyl. Examples of the aminocarbonylalkyl specifically include methylaminocarbonylmethyl, dimethylaminocarbonylmethyl, t-butylaminocarbonylmethyl, 1-azetidinylcarbonylmethyl, 1-pyrrolidinylcarbonylmethyl, 1-piperidinylcarbonylmethyl, 4-morpholinylcarbonylmethyl, 2-(methylaminocarbonyl)ethyl, 2-(dimethylaminocarbonyl)ethyl, 2-(1-azetidinylcarbonyl)ethyl, 2-(1-pyrrolidinylcarbonyl)ethyl, 2-(4-morpholinylcarbonyl)ethyl, 3-(dimethylaminocarbonyl)propyl, and 4-(dimethylaminocarbonyl)butyl.

In the present specification, the "aryloxyalkyl" means a group in which one or more hydrogen of the "alkyl" defined above are replaced with the "aryloxy" defined above, and is preferably $C_6$-$C_{10}$ aryloxy-$C_1$-$C_6$ alkyl, more preferably $C_6$-$C_{10}$ aryloxy-$C_1$-$C_2$ alkyl. Examples of the aryloxyalkyl specifically include phenoxymethyl and 2-phenoxyethyl.

In the present specification, the "aralkyl (arylalkyl)" means a group in which at least one hydrogen atom of the "alkyl" defined above is replaced with the "aryl" defined above, and is preferably $C_7$-$C_{14}$ aralkyl, more preferably $C_7$-$C_{10}$ aralkyl. Examples of the aralkyl specifically include benzyl, phenethyl, and 3-phenylpropyl.

In the present specification, the "aralkoxy" means an oxy group bonded to the "aralkyl" defined above and is preferably $C_7$-$C_{14}$ aralkoxy, more preferably $C_7$-$C_{10}$ aralkoxy. Examples of the aralkoxy specifically include benzyloxy, phenethyloxy, and 3-phenylpropoxy.

In the present specification, the "aralkoxyalkyl" means a group in which one or more hydrogen of the "alkyl" defined above are replaced with the "aralkoxy" defined above, and is preferably $C_7$-$C_{14}$ aralkoxy-$C_1$-$C_6$ alkyl, more preferably $C_7$-$C_{14}$ aralkoxy-$C_1$-$C_2$ alkyl. Examples of the aralkoxyalkyl specifically include benzyloxymethyl and 1-(benzyloxy) ethyl.

In the present specification, the "heteroarylalkyl" means a group in which at least one hydrogen atom of the "alkyl" defined above is replaced with the "heteroaryl" defined above, and is preferably 5- to 10-membered heteroaryl-$C_1$-$C_6$ alkyl, more preferably 5- to 10-membered heteroaryl-$C_1$-$C_2$ alkyl. Examples of the heteroarylalkyl specifically include 3-thienylmethyl, 4-thiazolylmethyl, 2-pyridylmethyl, 3-pyridylmethyl, 4-pyridylmethyl, 2-(2-pyridyl)ethyl, 2-(3-pyridyl)ethyl, 2-(4-pyridyl)ethyl, 2-(6-quinolyl)ethyl, 2-(7-quinolyl)ethyl, 2-(6-indolyl)ethyl, 2-(5-indolyl)ethyl, and 2-(5-benzofuranyl)ethyl.

In the present specification, the "heteroarylalkoxy" means an oxy group bonded to the "heteroarylalkyl" defined above and is preferably 5- to 10-membered heteroaryl-$C_1$-$C_6$ alkoxy, more preferably 5- to 10-membered heteroaryl-$C_1$-$C_2$ alkoxy. Examples of the heteroarylalkoxy specifically include 3-thienylmethoxy and 3-pyridylmethoxy.

In the present specification, the "heteroarylalkoxyalkyl" means a group in which one or more hydrogen of the "alkyl" defined above are replaced with the "heteroarylalkoxy" defined above, and is preferably 5- to 10-membered heteroaryl-$C_1$-$C_6$ alkoxy-$C_1$-$C_6$ alkyl, more preferably 5- to 10-membered heteroaryl-$C_1$-$C_2$ alkoxy-$C_1$-$C_2$ alkyl. Examples of the heteroarylalkoxyalkyl specifically include 3-pyridylmethoxymethyl.

In the present specification, the "heterocycloalkylidenealkyl" means a group in which one or more hydrogen of the "alkyl" defined above are replaced with the "heterocycloalkylidene" defined above, and is preferably 4- to 7-membered heterocycloalkylidene-$C_1$-$C_6$ alkyl, more preferably 4- to 7-membered heterocycloalkylidene-$C_1$-$C_2$ alkyl. Examples of the heteroarylalkoxyalkyl specifically include tetrahydro-4H-pyran-4-ylidenemethyl and azetidin-3-ylidenemethyl.

In the present specification, the "alkoxyalkenyl" means a group in which one or more hydrogen of the "alkenyl" defined above are replaced with the "alkoxy" defined above, and is preferably $C_1$-$C_6$ alkoxy-$C_2$-$C_6$ alkenyl. Examples of the alkoxyalkenyl specifically include (E)-4-methoxybut-2-en-1-yl.

In the present specification, the "aminocarbonylalkenyl" means a group in which one or more hydrogen of the "alkenyl" defined above are replaced with the "aminocarbonyl" defined above, and is preferably aminocarbonyl-$C_2$-$C_6$ alkenyl. Examples of the aminocarbonylalkenyl specifically include (E)-3-(dimethylaminocarbonylcarbonyl)-prop-2-en-1-yl.

In the present specification, the "haloalkoxy" means a group in which one or more hydrogen of the "alkoxy" defined above are replaced with halogen, and is preferably $C_1$-$C_6$ haloalkoxy. Examples of the haloalkoxy specifically include difluoromethoxy, trifluoromethoxy, 2,2-difluoroethoxy, and 2,2,2-trifluoroethoxy.

In the present specification, the "alkylene" means a divalent group induced by the further removal of one arbitrary hydrogen atom from the "alkyl" described above, and is preferably $C_4$-$C_8$ alkylene. Examples of the alkylene specifically include $—CH_2—$, $—(CH_2)_2—$, $—(CH_2)_3—$, $—CH(CH_3)CH_2—$, $—C(CH_3)_2—$, $—(CH_2)_4—$, $—CH(CH_3)CH_2CH_2—$, $—C(CH_3)_2CH_2—$, $—CH_2CH(CH_3)CH_2—$, $—CH_2C(CH_3)_2—$, $—CH_2CH_2CH(CH_3)—$, $—(CH_2)_5—$, $—(CH_2)_6—$, $—(CH_2)_7—$, and $—(CH_2)_8—$.

In the present specification, the "alicyclic ring" means a nonaromatic hydrocarbon ring. The alicyclic ring may have an unsaturated bond in the ring and may be a polycyclic ring having two or more rings. A carbon atom constituting the ring may form carbonyl through oxidation. The alicyclic ring is preferably a 3- to 8-membered alicyclic ring. Examples thereof specifically include a cyclopropane ring, a cyclobutane ring, a cyclopentane ring, a cyclohexane ring, a cycloheptane ring, a cyclooctane ring, and a bicyclo[2.2.1] heptane ring.

In the present specification, the "saturated heterocyclic ring" means a nonaromatic heterocyclic ring containing a carbon atom as well as 1 to 5 heteroatoms without containing a double bond and/or a triple bond in the ring. The saturated heterocyclic ring may be a monocyclic ring or may form a condensed ring with another ring, for example, an aromatic ring such as a benzene ring. When the saturated heterocyclic ring forms a condensed ring, the saturated heterocyclic ring is preferably a 4- to 7-membered saturated heterocyclic ring. Examples thereof specifically include an azetidine ring, an oxetane ring, a tetrahydrofuran ring, a tetrahydropyran ring, a morpholine ring, a thiomorpholine ring, a pyrrolidine ring, a 4-oxopyrrolidine ring, a piperidine ring, a 4-oxopiperidine ring, a piperazine ring, a pyrazolidine ring, an imidazolidine ring, an oxazolidine ring, an isoxazolidine ring, a thiazolidine ring, an isothiazolidine ring, a thiadiazolidine ring, an oxazolidone ring, a dioxolane ring, a dioxane ring, a thietane ring, an octahydroindole ring, and an indoline ring.

In the present specification, the "peptide chain" refers to a peptide chain of 1, 2, 3, 4, or more natural amino acids and/or non-natural amino acids linked through an amide bond and/or an ester bond. The peptide chain is preferably a peptide chain comprising 1 to 4 amino acid residues, more preferably a peptide chain consisting of 1 to 4 amino acid residues.

In the present specification, examples of the "protective group of an amino group" include a carbamate-type protective group, an amide-type protective group, an arylsulfonamide-type protective group, an alkylamine-type protective group, and an imide-type protective group, and specifically a Fmoc group, a Boc group, an Alloc group, a Cbz group, a Teoc group, a trifluoroacetyl group, a benzenesulfonyl group, a tosyl group, a nosyl group, a dinitronosyl group, a t-Bu group, a trityl group, a cumyl group, a benzylidene group, a 4-methoxybenzylidene group, and a diphenylmethylidene group.

In the present specification, examples of the "protective group for a carboxyl group" include an alkyl ester-type protective group, a benzyl ester-type protective group, and a substituted alkyl ester-type protective group. Examples of the protective group for a carboxyl group specifically include a methyl group, an ethyl group, a t-Bu group, a benzyl group, a trityl group, a cumyl group, a methoxytrityl group, a 2-(trimethylsilyl)ethyl group, a 2,2,2-trichloroethyl group, and an allyl group.

In the present specification, examples of the "protective group for a hydroxy" include an alkyl ether-type protective group, an aralkyl ether-type protective group, a silyl ether-type protective group and a carbonate ester-type protective group. Examples of the protective group for a hydroxy specifically include a methoxymethyl group, a benzyloxymethyl group, a tetrahydropyranyl group, a tert-butyl group, an allyl group, a 2,2,2-trichloroethyl group, a benzyl group, a 4-methoxybenzyl group, a trimethylsilyl group, a triethylsilyl group, a triisopropylsilyl group, a t-butyldimethylsilyl group, a t-butyldiphenylsilyl group, a methoxycarbonyl group, a 9-fluorenylmethoxycarbonyl group, and a 2,2,2-trichloroethoxycarbonyl group.

In the present specification, "optionally substituted" means that a group is optionally substituted by an arbitrary substituent.

In the present specification, "optionally protected" means that a group is optionally protected by an arbitrary protective group.

In the present specification, the term "one or more" means a number of 1 or 2 or larger. When the term "one or more" is used in a context related to a substituent for a certain group, this term means a number from 1 to the maximum number of substituents accepted by the group. Examples of the term "one or more" specifically include 1, 2, 3, 4, 5, 6, 7, 8, 9, 10, and/or larger numbers.

The salt of the compound of the present invention can be preferably a chemically or pharmaceutically acceptable salt. The compound of the present invention or the salt thereof can be a solvate thereof, preferably a chemically or pharmaceutically acceptable solvate thereof. Examples of the salt of the compound of the present invention include: hydrochloride; hydrobromide; hydroiodide; phosphate; phosphonate; sulfate; sulfonate such as methanesulfonate and p-toluenesulfonate; carboxylate such as acetate, citrate, malate, tartrate, succinate, and salicylate; alkali metal salts such as sodium salt, and potassium salt; alkaline earth metal salts such as magnesium salt and calcium salt; and ammonium salts such as ammonium salt, alkylammonium salt, dialkylammonium salt, trialkylammonium salt, and tetraalkylammonium salt. These salts are produced, for example, by bringing the compound into contact with an acid or base that can be used in the production of a medicament. In the present invention, the solvate of the compound refers to the phenomenon in which solute molecules strongly attract solvent molecules in solution to form a single molecular group, which is called a hydrate if the solvent is water. As the solvate of the compound of the present invention, a hydrate is preferable, and examples of such hydrate specifically include a 1- to 10-hydrate, preferably a 1- to 5-hydrate, and still more preferably a 1- to 3-hydrate. The solvate of the compound of the present invention includes not only solvates with a single solvent such as water, alcohols (e.g., methanol, ethanol, 1-propanol, and 2-propanol), and dimethylformamide, but also solvates with a plurality of solvents.

In the present specification, the "amino acid" includes a natural amino acid and a non-natural amino acid. In the present specification, the "natural amino acid" refers to Gly, Ala, Ser, Thr, Val, Leu, Ile, Phe, Tyr, Trp, His, Glu, Asp, Gln, Asn, Cys, Met, Lys, Arg, or Pro. Examples of the non-natural amino acid include, but are not particularly limited to, β-amino acids, γ-amino acids, D-amino acids, N-substituted amino acids, α,α-disubstituted amino acids, amino acids having a side chain different from the natural one, and hydroxycarboxylic acid. In the present specification, the amino acid accepts an arbitrary conformation. The side chain of the amino acid can be selected without particular limitations and is freely selected from a hydrogen atom as well as, for example, an alkyl group, an alkenyl group, an alkynyl group, an aryl group, a heteroaryl group, an aralkyl group, and a cycloalkyl group. One or two non-adjacent methylene groups in any of these groups may be substituted by an oxygen atom, a carbonyl group (—CO—), or a sulfonyl group ($—SO_2—$). A substituent may be added to each of the groups. Such a substituent is not limited and can be one or two or more substituents each independently freely selected from arbitrary substituents including a halogen atom, an O atom, a S atom, a N atom, a B atom, a Si atom, and a P atom. Specifically, examples thereof include an optionally substituted alkyl group, alkenyl group, alkynyl group, aryl group, heteroaryl group, aralkyl group, and cycloalkyl group. In a non-limiting aspect, the amino acid in the present specification may be a compound having a carboxy group and an amino group in the same molecule (even in this case, the amino acid also includes imino acids such as proline and hydroxyproline).

The backbone amino group of the amino acid may be unsubstituted ($NH_2$ group) or may be substituted (i.e., a —NHR group wherein R represents alkyl, alkenyl, alkynyl, aryl, heteroaryl, aralkyl, or cycloalkyl optionally having a substituent, and one or two non-adjacent methylene groups in any of these groups may be substituted by an oxygen atom, a carbonyl group (—CO—), or a sulfonyl group ($—SO_2—$); and a carbon chain bonded to a N atom and a carbon atom at position α may form a ring, as in proline). The substituent of R is selected in the same manner as in the substituent for the amino acid side chain mentioned above. In the case of a substituted backbone amino group, the R is contained in the "side chain of the amino acid" in the present specification. In the present specification, such an amino acid having the substituted backbone amino group is referred to as the "N-substituted amino acid". In the present specification, examples of the "N-substituted amino acid" preferably include, but are not limited to, N-alkyl amino acids, N—$C_1$-$C_6$ alkyl amino acids, N—$C_1$-$C_4$ alkyl amino acids, and N-methyl amino acids.

In the present specification, the "side chain of an amino acid" means, in the case of an α-amino acid, a group of atoms bound to the carbon (α-carbon) to which an amino group and a carboxyl group are bound. For example, the methyl group of Ala is a side chain of an amino acid. In the case of a β-amino acid, the group of atoms bound to the α-carbon and/or β-carbon can be a side chain of the amino acid, and in the case of a γ-amino acid, the group of atoms bound to the α-carbon, β-carbon, and/or γ-carbon can be a side chain of the amino acid.

In the present specification, the "main chain of an amino acid" means, in the case of an α-amino acid, a chain portion consisting of an amino group, an α-carbon, and a carboxyl group; in the case of a β-amino acid, a chain portion consisting of an amino group, a β-carbon, an α-carbon, and a carboxyl group; and in the case of a γ-amino acid, a chain portion consisting of an amino group, a γ-carbon, a β-carbon, an α-carbon, and a carboxyl group.

In the present specification, the "main chain of a peptide", "main chain of a peptide compound" and "main chain of a cyclic peptide compound" means a structure formed by linking a plurality of the above "main chains of amino acids" by amide bonds.

In the present specification, the "amino acid" constituting the peptide compound includes all isotopes corresponding to each amino acid. The isotope of the "amino acid" is a form in which at least one atom is replaced with an atom having the same atomic number (proton number) therewith and a different mass number (total number of protons and neutrons) therefrom. Examples of the isotope included in the "amino acid" constituting the peptide compound of the present invention include a hydrogen atom, a carbon atom, a nitrogen atom, an oxygen atom, a phosphorus atom, a sulfur atom, a fluorine atom, and a chlorine atom, and they include $^{2}H$, $^{3}H$; $^{13}C$, $^{14}C$; $^{15}N$; $^{17}O$, $^{18}O$; $^{31}P$; $^{32}P$; $^{35}S$; $^{18}F$; and $^{36}Cl$, respectively.

In the present specification, examples of the substituent containing a halogen atom include an alkyl group, a cycloalkyl group, an alkenyl group, an alkynyl group, an aryl group, a heteroaryl group, and an aralkyl group having halogen as a substituent and more specifically include fluoroalkyl, difluoroalkyl, and trifluoroalkyl.

Examples of substituents containing an O atom include groups such as hydroxy (—OH), oxy (—OR), carbonyl (—C═O—R), carboxy (—$CO_2$H), oxycarbonyl (—C═O—OR), carbonyloxy (—O—C═O—R), thiocarbonyl (—C═O—SR), a carbonylthio (—S—C═O—R), aminocarbonyl (—C═O—NHR), carbonylamino (—NH—C═O—R), oxycarbonylamino (—NH—C═O—OR), sulfonylamino (—NH—$SO_2$—R), aminosulfonyl (—$SO_2$—NHR), sulfamoylamino (—NH—$SO_2$—NHR), thiocarboxyl (—C(═O)—SH), and carboxylcarbonyl (—C(═O)—$CO_2$H).

Examples of the oxy (—OR) include alkoxy, cycloalkoxy, alkenyloxy, alkynyloxy, aryloxy, heteroaryloxy, and aralkyloxy. The alkoxy is preferably $C_1$-$C_4$ alkoxy or $C_1$-$C_2$ alkoxy, particularly preferably methoxy or ethoxy.

Examples of the carbonyl (—C═O—R) include formyl (—C═O—H), alkylcarbonyl, cycloalkylcarbonyl, alkenylcarbonyl, alkynylcarbonyl, arylcarbonyl, heteroarylcarbonyl, and aralkylcarbonyl.

Examples of the oxycarbonyl (—C═O—OR) include alkyloxycarbonyl, cycloalkyloxycarbonyl, alkenyloxycarbonyl, alkynyloxycarbonyl, aryloxycarbonyl, heteroaryloxycarbonyl, and aralkyloxycarbonyl.

Examples of the carbonyloxy (—O—C═O—R) include alkylcarbonyloxy, cycloalkylcarbonyloxy, alkenylcarbonyloxy, alkynylcarbonyloxy, arylcarbonyloxy, heteroarylcarbonyloxy, and aralkylcarbonyloxy.

Examples of the thiocarbonyl (—C═O—SR) include alkylthiocarbonyl, cycloalkylthiocarbonyl, alkenylthiocarbonyl, alkynylthiocarbonyl, arylthiocarbonyl, heteroarylthiocarbonyl, and aralkylthiocarbonyl.

Examples of the carbonylthio (—S—C═O—R) include alkylcarbonylthio, cycloalkylcarbonylthio, alkenylcarbonylthio, alkynylcarbonylthio, arylcarbonylthio, heteroarylcarbonylthio, and aralkylcarbonylthio.

Examples of the aminocarbonyl (—C═O—NHR) include alkylaminocarbonyl (e.g., $C_1$-$C_6$ or $C_1$-$C_4$ alkylaminocarbonyl, particularly, ethylaminocarbonyl and methylaminocarbonyl), cycloalkylaminocarbonyl, alkenylaminocarbonyl, alkynylaminocarbonyl, arylaminocarbonyl, heteroarylaminocarbonyl, and aralkylaminocarbonyl. Examples thereof additionally include groups in which the H atom bonded to the N atom in —C═O—NHR is further replaced with alkyl, cycloalkyl, alkenyl, alkynyl, aryl, heteroaryl, or aralkyl.

Examples of the carbonylamino (—NH—C═O—R) include alkylcarbonylamino, cycloalkylcarbonylamino, alkenylcarbonylamino, alkynylcarbonylamino, arylcarbonylamino, heteroarylcarbonylamino, and aralkylcarbonylamino. Examples thereof additionally include groups in which the H atom bonded to the N atom in —NH—C═O—R is further replaced with alkyl, cycloalkyl, alkenyl, alkynyl, aryl, heteroaryl, or aralkyl.

Examples of the oxycarbonylamino (—NH—C═O—OR) include alkoxycarbonylamino, cycloalkoxycarbonylamino, alkenyloxycarbonylamino, alkynyloxycarbonylamino, aryloxycarbonylamino, hetermaryloxycarbonylamino, and aralkyloxycarbonylamino. Examples thereof additionally include groups in which the H atom bonded to the N atom in —NH—C═O—OR is further replaced with alkyl, cycloalkyl, alkenyl, alkynyl, aryl, heteroaryl, or aralkyl.

Examples of the sulfonylamino (—NH—$SO_2$—R) include alkylsulfonylamino, cycloalkylsulfonylamino, alkenylsulfonylamino, alkynylsulfonylamino, arylsulfonylamino, heteroarylsulfonylamino, and aralkylsulfonylamino. Examples thereof additionally include groups in which the H atom bonded to the N atom in —NH—$SO_2$—R is further replaced with alkyl, cycloalkyl, alkenyl, alkynyl, aryl, heteroaryl, or aralkyl.

Examples of the aminosulfonyl (—$SO_2$—NHR) include alkylaminosulfonyl, cycloalkylaminosulfonyl, alkenylaminosulfonyl, alkynylaminosulfonyl, arylaminosulfonyl, heteroarylaminosulfonyl, and aralkylaminosulfonyl. Examples thereof additionally include groups in which the H atom bonded to the N atom in —$SO_2$—NHR is further replaced with alkyl, cycloalkyl, alkenyl, alkynyl, aryl, heteroaryl, or aralkyl.

Examples of the sulfamoylamino (—NH—$SO_2$—NHR) include alkylsulfamoylamino, cycloalkylsulfamoylamino, alkenylsulfamoylamino, alkynylsulfamoylamino, arylsulfamoylamino, heteroarylsulfamoylamino, and aralkylsulfamoylamino. The two H atoms bonded to the N atoms in —NH—$SO_2$—NHR may be substituted by substituents each independently selected from the group consisting of alkyl, cycloalkyl, alkenyl, alkynyl, aryl, heteroaryl, and aralkyl, and these two substituents may form a ring.

Examples of the substituent containing a S atom include groups such as thiol (—SH), thio (—S—R), sulfinyl (—S═O—R), sulfonyl (—$SO_2$—R), and sulfo (—$SO_3$H).

Examples of the thio (—S—R) that can be selected include alkylthio, cycloalkylthio, alkenylthio, alkynylthio, arylthio, heteroarylthio, and aralkylthio.

Examples of the sulfonyl (—$SO_2$—R) include alkylsulfonyl, cycloalkylsulfonyl, alkenylsulfonyl, alkynylsulfonyl, arylsulfonyl, heteroarylsulfonyl, and aralkylsulfonyl.

Examples of the substituent containing a N atom include groups such as azide (—$N_3$; also referred to as an "azide group"), cyano (—CN), primary amino (—$NH_2$), secondary amino (—NH—R; also referred to as mono-substituted amino), tertiary amino (—NR(R'); also referred to as di-substituted amino), amidino (—C(═NH)—$NH_2$), substituted amidino (—C(═NR)—NR'R"), guanidino (—NH—C(═NH)—$NH_2$), substituted guanidino (—NR—C(═NR'")—NR'R"), aminocarbonylamino (—NR—CO—NR'R"), pyridyl, piperidino, morpholino, and azetidinyl.

Examples of the secondary amino (—NH—R: mono-substituted amino) include alkylamino, cycloalkylamino, alkenylamino, alkynylamino, arylamino, heteroarylamino, and aralkylamino.

Examples of the tertiary amino (—NR(R'): di-substituted amino) include an amino group having arbitrary two substituents each independently selected from alkyl, cycloalkyl, alkenyl, alkynyl, aryl, heteroaryl, and aralkyl, for example, alkyl(aralkyl)amino. These arbitrary two substituents may form a ring. Examples thereof specifically include dialkylamino, particularly, $C_1$-$C_6$ dialkylamino, $C_1$-$C_4$ dialkylamino, dimethylamino, and diethylamino. In the present specification, the "$C_p$-$C_q$ dialkylamino group" refers to a group in which an amino group is substituted by two $C_p$-$C_q$ alkyl groups. The $C_p$-$C_q$ alkyl groups may be the same or different.

Examples of the substituted amidino (—C(═NR)—NR'R") include groups in which three substituents R, R', and R" on the N atoms are each independently selected from alkyl, cycloalkyl, alkenyl, alkynyl, aryl, heteroaryl, and aralkyl, for example, alkyl(aralkyl)(aryl)amidino.

Examples of the substituted guanidino (—NR—C(═NR'")—NR'R") include groups in which R, R', R", and R'" are each independently selected from alkyl, cycloalkyl, alkenyl, alkynyl, aryl, heteroaryl, and aralkyl, and groups in which these substituents form a ring.

Examples of the aminocarbonylamino (—NR—CO—NR'R") include groups in which R, R', and R" are each independently selected from a hydrogen atom, alkyl, cycloalkyl, alkenyl, alkynyl, aryl, heteroaryl, and aralkyl, and groups in which these substituents form a ring.

In the present specification, the "amino acid residue" constituting the peptide compound is also simply referred to as an "amino acid".

In the present specification, the "linear peptide compound" is formed by natural amino acids and/or non-natural amino acids linked by amide or ester bonds, and is not particularly limited as long as it is a compound that does not have a cyclic portion. The total number of natural or non-natural amino acids constituting a linear peptide compound can be 1, 2, 3, 4, 5, 6, 7, 8, 9, 10, 11, 12, 13, 14, 15, 20, 25, or 30, and preferable ranges are 6 to 20, 7 to 19, 7 to 18, 7 to 17, 7 to 16, 7 to 15, 8 to 14, and 9 to 13.

In the present specification, the "cyclic peptide compound" is formed by natural amino acids and/or non-natural amino acids linked by amide or ester bonds, and is not particularly limited as long as it is a compound that has a cyclic portion. The total number of natural or non-natural amino acids constituting a cyclic peptide compound can be 1, 2, 3, 4, 5, 6, 7, 8, 9, 10, 11, 12, 13, 14, 15, 20, 25, or 30, and preferable ranges are 6 to 20, 7 to 19, 7 to 18, 7 to 17, 7 to 16, 7 to 15, 8 to 14, and 9 to 13.

In the present specification, the "cyclic portion" of a peptide compound means a cyclic portion formed by the linking of two or more amino acid residues. In the present specification, the "linear portion" used to refer to the substructure of a cyclic peptide compound refers to a portion that is not included in the main chain structure of the cyclic portion and that has at least one amide and/or ester bond on the chain of that portion.

In the present specification, the number of amino acids constituting the cyclic portion of a cyclic peptide compound is not limited, but examples thereof include 2 or more, 3 or more, 4 or more, 6 or more, 7 or more, 8 or more, 9 or more, 10 or more, 11 or more, 12 or more, 30 or less, 20 or less, 18 or less, 16 or less, 15 or less, 14 or less, 13 or less, 12 or less, 11 or less, 7, 8, 9, 10, 11, 12, 13, 14, 15, and 16. Considering both membrane permeability and metabolic stability, the number of amino acids constituting the cyclic portion is preferably 2 to 30, 2 to 15, or 5 to 15, more preferably 5 to 14, 7 to 14, or 8 to 14, still more preferably 8 to 13, 9 to 13, 8 to 12, 8 to 11, or 9 to 12, and particularly preferably 9 to 11.

In a certain aspect, the number (number of units) of amino acids in the linear portion is preferably 0 to 8, more preferably 0 to 5, and more preferably 0 to 3. In a non-limiting aspect, the "linear portion" in the present specification may include natural and non-natural amino acids (including chemically modified or skeletally converted amino acids).

In a certain aspect, the molecular weight of a cyclic peptide compound in the present specification can be 500 to 2000.

In the present specification, the "peptide compound" may include a pharmaceutically acceptable salt thereof, or a solvate thereof.

In the present specification, the "side chain" is used in the context of a side chain of an amino acid, or a side chain of the cyclic portion of a cyclic peptide compound, and means a portion not included in the respective main chain structure.

In the present specification, the "number of amino acids" refers to the number of amino acid residues (amino acid units) constituting a peptide compound, and means the number of amino acid units that result when the amide bonds, ester bonds, and bonds at the cyclization portion linking the amino acids to each other are cleaved.

In the present specification, the "degradation of an amino acid" includes any structural transformation in which the original amino acid structure is not maintained.

In the present specification, the "degradation of a peptide" includes any structural transformation in which the original peptide structure is not maintained, including transfers of functional groups in the main and side chains.

In the present specification, the "degradation of the resin for solid-phase synthesis" includes physical degradation, in which the solid resin changes to a state in which it does not maintain its original shape, as well as changes to states in which it does not maintain its function of loading amino acids or peptides, partially or at all.

In the present specification, the "loading ratio" is calculated from the amino acids that could be loaded on the resin for solid-phase synthesis in the loading reaction, based on the amount of amino acid used as the starting material, and means the reaction conversion ratio.

In the present specification, the "reaction conversion ratio" means the ratio of amino acids in solution converted to the state of being loaded on the resin for solid-phase synthesis, and can be calculated from the concentration of amino acids in the reaction solution before the start and after the end of the loading reaction of the amino acids on the resin for solid-phase synthesis. Specifically, the reaction conversion ratio can be calculated by the following formula using the measurement conditions described in the Examples.

Reaction Conversion Ratio (%)={(area of amino acids before start of loading reaction)−(area of amino acids after end of loading reaction)}×100/area of amino acids before start of loading reaction Herein, the meaning of the term "and/or" includes any combination in which "and" and "or" are appropriately combined. Specifically, for example, "A, B, and/or C" includes the following seven variations:

(i) A, (ii) B, (iii) C, (iv) A and B, (v) A and C, (vi) B and C, and (vii) A, B, and C.

In a certain aspect, the present invention relates to a method for producing a peptide compound comprising at least one N-substituted amino acid, a salt thereof, or a solvate thereof, the method comprising a step of bringing a resin for solid-phase synthesis swollen in a solvent comprising a first solvent into contact with (i) a solution comprising an amino acid and a second solvent, or (ii) a solution comprising an amino acid, a second solvent, and a third solvent, to obtain an amino acid loaded on the resin for solid-phase synthesis (Step 1). In this method, the first solvent and the third solvent are each independently selected from halogenated solvents. The second solvent is an ether solvent.

In a certain aspect, the present invention relates to a method for producing an amino acid loaded on a resin for solid-phase synthesis, the method comprising a step of bringing a resin for solid-phase synthesis swollen in a solvent comprising a first solvent into contact with (i) a solution comprising an amino acid and a second solvent, or (ii) a solution comprising an amino acid, a second solvent, and a third solvent. In this method, the first solvent and the third solvent are each independently selected from halogenated solvents. The second solvent is an ether solvent.

In the solid-phase method, in order to efficiently load amino acids on the resin for solid-phase synthesis, the resin for solid-phase synthesis is usually swollen with a solvent prior to the loading reaction of amino acids on the resin. In the present invention, a solvent containing a first solvent selected from halogenated solvents is used to swell the resin for solid-phase synthesis. Examples of the first solvent specifically include DCM, DCE, chloroform, chlorobenzene, and carbon tetrachloride, of which DCM is preferred. If the first solvent contains another solvent in addition to a halogenated solvent, any solvent, such as MeTHF, MTBE, CPME, THF, IPE, DME, diethyl ether, or dioxane, can be contained in addition to the halogenated solvent. As a solvent contained in addition to the halogenated solvent, MeTHF, MTBE, and CPME are preferred. For these solvents, dehydrated solvents are preferably used for the purpose of suppressing the degradation of the resin for solid-phase synthesis. The dehydrated solvent may be a commercially available dehydrated solvent that can be purchased from a commercial supplier, or a solvent that has been dehydrated beforehand by any method. The swelling of the resin for solid-phase synthesis can be performed by adding a solvent containing the first solvent to a container such as a column containing the resin, and maintaining this state at any temperature, for example, room temperature, for any period of time, for example, 5 minutes to 24 hours, during which the container may be shaken. Once the swelling of the resin is complete, the solvent is preferably discharged from the container by filtration or the like.

In a certain aspect, once the resin for solid-phase synthesis has sufficiently swelled, the amino acids can be loaded on the resin for solid-phase synthesis by bringing the resin for solid-phase synthesis into contact with a solution containing the amino acids and a second solvent. The loading of the amino acids on the resin for solid-phase synthesis is usually performed by linking the carboxyl groups of the amino acids to the linker atom groups contained in the resin. The second solvent is an ether solvent such as MeTHF, MTBE, CPME, THF, IPE, DME, diethyl ether, or dioxane, of which MeTHF, MTBE, and CPME are preferred. The solution preferably does not contain any solvents other than the second solvent. The contact of the resin for solid-phase synthesis with the solution containing the amino acids and the second solvent can be performed, for example, by adding a solution containing the amino acids and the second solvent to a container such as a column containing the resin, and maintaining this state at any temperature, for example, room temperature, for any period of time, for example, 10 minutes to 24 hours, during which the container may be shaken. The concentration of amino acids in the solution is not particularly limited, but preferred examples include the range of 0.01 mol/L to 2.0 mol/L. If an acid is produced by the loading reaction between a linker atom group and an amino acid, a base such as DIPEA can be added to the solution to capture the acid.

In another aspect, once the resin for solid-phase synthesis has sufficiently swelled, the amino acids can be loaded on the resin for solid-phase synthesis by bringing the resin for solid-phase synthesis into contact with a solution containing the amino acids and a mixed solvent of the second solvent and the third solvent. The second solvent is an ether solvent such as MeTHF, MTBE, CPME, THF, IPE, DME, diethyl ether, and dioxane, of which MeTHF, MTBE, and CPME are preferred. The third solvent is a halogenated solvent such as DCM, DCE, chloroform, chlorobenzene, and carbon tetrachloride, of which DCM is preferred. The mixing ratio of the second solvent with the third solvent is not particularly limited, but their volume ratio is preferably in the range of 1:1 to 1:10, and examples thereof specifically include second solvent:third solvent=1:1, 1:2, 1:5, and 1:10. Preferred combinations of the second solvent and the third solvent include MeTHF and DCM, MTBE and DCM, CPME and DCM, MeTHF and DCE, THF and DCM, and WE and DCM. The solution preferably does not contain any solvents other than the second solvent and the third solvent. The contact of the resin for solid-phase synthesis with a solution containing the amino acids and the mixed solvent of the second solvent and the third solvent can be performed, for example, by adding a solution containing the amino acids and the second solvent or third solvent, then adding the third solvent or second solvent, or adding a solution containing the amino acids and the mixed solvent of the second solvent and the third solvent, to a container such as a column containing the resin, and maintaining this state at any temperature, for example, room temperature, for any period of time, for example, 10 minutes to 24 hours, during which the container may be shaken. The concentration of amino acids in the solution is not particularly limited, but preferred examples include the range of 0.01 mol/L to 2.0 mol/L. If an acid is produced by the loading reaction between a linker atom group and an amino acid, a base such as DIPEA can be added to the solution to capture the acid.

According to the present invention, which uses a specific solvent for the swelling of the resin for solid-phase synthesis and the subsequent loading of amino acids on the resin, the amino acids can be linked to the resin at a very high loading ratio or reaction conversion ratio, such as a loading ratio or reaction conversion ratio of 90% or more, 91% or more, 92% or more, 93% or more, 94% or more, 95% or more, 96% or more, 97% or more, 98% or more, 99% or more, or about 100%.

The "resin for solid-phase synthesis" used in the present invention is not particularly limited as long as it can be used for the synthesis of peptide compounds by the solid-phase method. Examples of such resin for solid-phase synthesis specifically include those that can be removed under acidic conditions, such as a CTC resin, a Wang resin, a SASRIN resin, a trityl chloride resin (Trt resin), a 4-methyltrityl chloride resin (Mtt resin), and 4-methoxytrityl chloride resin (Mmt). The resin can be appropriately selected according to the functional group on the amino acid used. For example, if a carboxyl group (main-chain carboxyl group or side-chain carboxyl group typified by Asp or Glu) or a hydroxy group on an aromatic ring (phenolic hydroxyl group typified by Tyr) is used as the functional group on the amino acid, a trityl chloride resin (Trt resin) or a 2-chlorotrityl chloride resin (CTC resin) is preferably used as the resin. If an aliphatic hydroxy group (aliphatic alcoholic hydroxyl group typified by Ser and Thr) is used as the functional group on the amino acid, a trityl chloride resin (Trt resin), a 2-chlorotrityl chloride resin (CTC resin) or a 4-methyltrityl chloride resin (Mtt resin) is preferably used as the resin. In the present specification, resin is sometimes referred to as resin.

The type of polymer constituting the resin is also not particularly limited. In the case of a resin composed of polystyrene, either 100-200 mesh or 200-400 mesh may be used. The cross-linking ratio is not particularly limited, but 1% cross-linked with DVB (divinylbenzene) is preferred. Examples of the type of polymer constituting the resin include TentaGel (registered trademark) and ChemMatrix (registered trademark).

In a certain aspect, the amino acid to be loaded on the resin for solid-phase synthesis in the present invention may be a natural amino acid or a non-natural amino acid. If the amino acid to be loaded on the resin for solid-phase synthesis is a non-natural amino acid, the amino acid is preferably a non-natural N-substituted amino acid. The non-natural amino acid can contain an aminocarbonyl group such as mono-$C_1$-$C_6$ alkylaminocarbonyl, di-$C_1$-$C_6$ alkylaminocarbonyl, and 4- to 8-membered cyclic aminocarbonyl. Examples of such aminocarbonyl group specifically include dimethylaminocarbonyl, 1-azetidinylcarbonyl, 1-pyrrolidinylcarbonyl, 1-piperidinylcarbonyl, 1-piperazinylcarbonyl, 4-morpholinylcarbonyl, 3-oxazolidinylcarbonyl, 1,1-dioxidothiomorpholinyl-4-ylcarbonyl, and 3-oxa-8-azabicyclo[3.2.1]octane-8-ylcarbonyl, and these groups are preferably present on a side chain. The amino acid to be loaded on the resin for solid-phase synthesis preferably has its amino group protected with a protective group.

The amino acid is loaded on the resin for solid-phase synthesis by a carboxyl group bound to the carbon atom at the α, β, or γ-position of the amino group. Examples of amino acids loaded on the resin for solid-phase synthesis by a carboxyl group bound to the carbon atom at the β-position of the amino group include aspartic acid and derivatives thereof. Specifically, the case in which it is loaded on the resin for solid-phase synthesis by the carboxyl group present in the side chain of aspartic acid corresponds to the case in which it is loaded on the resin for solid-phase synthesis by the carboxyl group bound to the carbon atom at the β-position of the amino group. In addition, examples of amino acids loaded on the resin for solid-phase synthesis by a carboxyl group bound to the carbon atom at the γ-position of the amino group include glutamic acid and derivatives thereof. Specifically, the case in which it is loaded on the resin for solid-phase synthesis by the carboxyl group present in the side chain of glutamic acid corresponds to the case in which it is loaded on the resin for solid-phase synthesis by the carboxyl group bound to the carbon atom at the γ-position of the amino group. Other natural amino acid residues and the N-substituted amino acid residues thereof are usually loaded on the resin for solid-phase synthesis by a carboxyl group bound to the carbon atom at the α-position of the amino group.

In a certain aspect, the non-natural amino acid loaded on the resin for solid-phase synthesis by a carboxyl group bound to the carbon atom at the β-position of the amino group is aminocarbonylated aspartic acid, 2-aminobutanoic acid, or an N-substituted form thereof. Here, aminocarbonylated aspartic acid is aminocarbonylated (—CONRR') at the free carboxyl (—COOH) group bound to the carbon atom at the α-position of the amino group of aspartic acid. Examples of aminocarbonylated aspartic acid specifically include dialkylaminocarbonylated aspartic acid such as dimethylaminocarbonyl, in other words, aspartic acid in which the R and R' are independently alkyl groups, and aspartic acid aminocarbonylated with the N atom of a saturated heterocyclic ring containing an N atom (e.g., azetidine ring, morpholine ring, pyrrolidine ring, piperidine ring, and azepane ring), in other words, aspartic acid in which R and R' together with the N atom to which they are bound form a saturated heterocyclic ring, and these can be N-substituted forms, such as N-alkyl forms including N-methyl and N-ethyl forms.

In a certain aspect, the non-natural amino acid loaded on the resin for solid-phase synthesis by a carboxyl group bound to the carbon atom at the γ-position of the amino group is aminocarbonylated glutamic acid, or an N-substituted form thereof. Here, aminocarbonylated glutamic acid is aminocarbonylated (—CONRR') at the free carboxyl (—COOH) group of glutamic acid. Examples of aminocarbonylated glutamic acid specifically include dialkylaminocarbonylated glutamic acid such as dimethylaminocarbonyl, in other words, aspartieglutamic acid in which the R and R' are independently alkyl groups, and glutamic acid aminocarbonylated with the N atom of a saturated heterocyclic ring containing an N atom (e.g., azetidine ring, morpholine ring, pyrrolidine ring, piperidine ring, and azepane ring), in other words, aspartieglutamic acid in which R and R' together with the N atom to which they are bound form a saturated heterocyclic ring, and these can be N-substituted forms, such as N-alkyl forms including N-methyl and N-ethyl forms.

In a certain aspect, the first solvent used for swelling the resin for solid-phase synthesis and the third solvent used for loading the amino acids on the resin are preferably the same solvent. That is, if a mixed solvent of the second solvent and the third solvent is used in the reaction for loading the amino acids on the resin for solid-phase synthesis, the third solvent can be the same solvent as the solvent used for swelling the resin for solid-phase synthesis. If the first solvent and the third solvent are the same solvent, DCM is preferred as the solvent.

In a certain aspect, the solution containing an amino acid and the second solvent can be a solution obtained by an extraction operation including the use of a second solvent, which is performed after the deprotection reaction of the protective group for the amino acid's carboxyl group prior to step 1, and a subsequent optional dehydration operation.

In another aspect, the solution containing an amino acid, a second solvent, and a third solvent can be a solution obtained by further adding a third solvent to a solution obtained by an extraction operation including the use of a second solvent, which is performed after the deprotection reaction of the protective group for the amino acid's carboxyl group prior to step 1, and a subsequent optional dehydration operation.

If the amino acid to be loaded on the resin for solid-phase synthesis is provided as an amino acid in which the carboxyl group or both the amino and carboxyl groups are protected with a protective group, the protective group of the carboxyl group needs to be removed for deprotection prior to the loading reaction on the resin to prepare for linkage with the linker atom group of the resin. In the present invention, by subjecting the amino acid produced after the deprotection reaction for that purpose to an extraction operation including the use of a second solvent, a "solution containing the amino acid and the second solvent" to be used for the loading reaction on the resin for solid-phase synthesis can be obtained without isolating or purifying the amino acid. Alternatively, by adding a third solvent to the "solution containing the amino acid and the second solvent" thus obtained, a "solution containing the amino acid, the second solvent, and the third solvent" to be used for the loading reaction on the resin for solid-phase synthesis can be obtained. After the extraction operation, a dehydration operation may be performed, for which a desiccant such as $Na_2SO_4$, $MgSO_4$, or $CaCl_2$) is preferably used. When isolating and purifying deprotected amino acids, operations such as solvent distillation and azeotropic dehydration are required, and as such, the amino acids are kept in solution for a long time, which promotes their degradation. This tendency is even more pronounced in large-scale synthesis, where the amount of solvent and reagents is increased. By using the above method of the present invention, which does not involve the isolation and purification of deprotected amino acids, it is possible to avoid such problems and to effectively link to the subsequent loading reaction. For the removal of the protective group for the carboxyl group, known methods, such as those described in Greene's, "Protective Groups in Organic Synthesis" (5th edition, John Wiley & Sons 2014), can be used. After the deprotection reaction, any operation commonly used in the present art, such as a reaction stopping operation, a back-extraction operation in which the target product is once transferred to an aqueous layer, or a washing operation of the organic or aqueous layer, may be included before or after the extraction operation including the use of a second solvent. If a back-extraction operation is performed, the "solution containing the amino acid and the second solvent" can be obtained by adding an acid (e.g., phosphoric acid) and the second solvent to the aqueous layer from which the organic layer after the back-extraction operation has been removed, and extracting the product.

If the carboxyl group of the amino acid is protected with a protective group, the protective group is preferably removable by an acid. Examples of such protective group specifically include t-Bu, trityl, methoxytrityl, and cumyl. As the acid capable of removing the protective group, the acids in the acidic conditions described in Greene's, "Protective Groups in Organic Synthesis" (5th edition, John Wiley & Sons 2014), and those described in WO 2020/111238 can be used.

In a certain aspect, the present invention further includes a step of elongating one or more arbitrary amino acids to the amino acid loaded on the resin for solid-phase synthesis. This step allows to obtain a peptide compound with the desired amino acid sequence. Methods known in the present art can be used for this step, and for example, the methods described in WO 2013/100132, WO 2018/225851, and WO 2018/225864, or the method described in the Solid Phase Synthesis Handbook published by Merck on May 1, 2002 can be applied.

In a certain aspect, the "peptide compound" of the present invention produced by the solid-phase method is a linear peptide compound, which, in addition to the conditions for the total number of natural and non-natural amino acids described above, contains at least one N-substituted amino acid residue, preferably at least two (specifically 2, 3, 4, 5, 6, 7, 8, 9, 10, 11, 12, 13, 14, 15, 20, 25, or 30, preferably 5, 6 or 7, with preferred ranges of 2 to 30, 3 to 30, 6 to 20, 7 to 19, 7 to 18, 7 to 17, 7 to 16, 7 to 15, 8 to 14, and 9 to 13), and contains at least one amino acid residue that is not N-substituted. Examples of the percentage of N-substituted amino acids in such peptide compound include 30% or more, 40% or more, 50% or more, 60% or more, 70% or more, and 80% or more of the total number of amino acids constituting the peptide compound. The N-substituted amino acid residue in the present invention may be a non-natural N-substituted amino acid residue other than proline.

In a certain aspect, the present invention also relates to a method for producing a cyclic peptide compound, which further includes a step of obtaining a linear peptide compound, a salt thereof, or a solvate thereof produced by the solid-phase method, a step of removing the resin for solid-phase synthesis, and a step of cyclizing the C-terminus group and the N-terminus group of the peptide compound to form a cyclic portion.

For both the step of removing the peptide compound from the resin for solid-phase synthesis and the step of cyclizing the C-terminus group and the N-terminus group of the peptide compound to form a cyclic portion, methods known in the present art can be used, and for example, the methods described in WO 2013/100132, WO 2018/225851, and WO 2018/225864, or the methods described in the Solid Phase Synthesis Handbook published by Merck on May 1, 2002 can be applied.

In a certain aspect, the number of N-substituted amino acids in the cyclic portion of the cyclic peptide compound is preferably 2 or more or 3 or more, more preferably 4 or more, 5 or more, or 6 or more, still more preferably 7 or more, particularly preferably 8 or more, and 20 or less, 15 or less, 14 or less, 13 or less, 12 or less, 10 or less, and 9 or less are also preferred examples. In the present specification, examples of the number of N-substituted amino acids in the cyclic peptide compound include 30% or more, 40% or more, 50% or more, 60% or more, 70% or more, and 80% or more of the number of amino acids constituting the cyclic portion.

The compound of the present invention, the salt thereof, or the solvate thereof includes all stereoisomers of the compound of interest obtained through each of the reaction steps described above (e.g., enantiomers, diastereomers (including cis and trans geometric isomers)), racemates of the isomers, and other mixtures. For example, the compound of the present invention may have one or more asymmetric points, and the present invention includes racemic mixtures, diastereomeric mixtures, and enantiomers of such compound.

If the compound according to the present invention is obtained as a free form, the compound can be converted to a state of salt, or hydrate or solvate thereof, that may be formed by the compound, according to a conventional method.

If the compound according to the present invention is obtained as a salt, hydrate, or solvate of the compound, the compound can be converted to its free form according to a conventional method.

All references cited herein are incorporated herein by reference.

EXAMPLES

The contents of the present invention are further described by the following Examples, but the present invention is not limited to these contents. All starting materials and reagents were obtained from commercial suppliers or synthesized using known methods.

[Quantitation Method]

The method for evaluating the loading ratio on the resin for solid-phase synthesis was calculated based on the reaction conversion ratio shown below. That is, the reaction conversion ratio for the loading reaction was calculated based on the amount of reduction obtained by comparing the amount of amino acids in the reaction solution before the start of the loading reaction and the amount of amino acids in the reaction solution after the end of the loading reaction. The amount of amino acids was calculated by measuring the amino acid concentration in the reaction solution by the method shown below. Specifically, the solution after the end of the loading reaction was filtered, 5 μL of the filtrate was diluted with 1 mL of acetonitrile, and then 1 μL of the diluted solution was used for HPLC measurements. If an aspartic acid derivative was used as the amino acid, the calculation was made according to the following formula.

Reaction Conversion Ratio (%)={(area of aspartic acid derivative before start of loading reaction)−(area of aspartic acid derivative after end of loading reaction)}×100/area of aspartic acid derivative before start of loading reaction The yield in the loading reaction was calculated by the Fmoc quantitation method or by a method of performing a deresination treatment on the resin after the loading reaction and measuring the weight of the recovered amino acids (isolation method).

The Fmoc quantitation method is a method in which the Fmoc groups of Fmoc amino acids loaded for solid-phase synthesis are removed and the amount of Fmoc is calculated from the absorbance of free dibenzofulvene. The operations for the Fmoc quantitation method are as follows.

Approximately 15 mg of dried resin was weighed precisely and made up to 100 mL by adding a 20% piperidine DMF solution. After shaking for 30 minutes or more, approximately 1 mL of the solution was measured by a spectrophotometer.

The yield determined by the Fmoc quantitation method was calculated according to the following formula.

Loading rate=((absorption value at 289.8 nm wavelength)/6089)×100000/(weight of weighed dry resin)

Yield (Fmoc quantitation method)=(total weight of dry resin)×(loading rate)×(molecular weight of loaded amino acid)×100/(weight of loaded amino acid)

Operation for isolation method: A resin for solid-phase synthesis loading amino acids was swollen with DMF. The above resin for solid-phase synthesis was mixed with a DCM solution containing TFA to perform a deresination reaction of the amino acids loaded on the resin for solid-phase synthesis. The resin for solid-phase synthesis and the solution were separated, and the solvent of the solution was distilled off to measure the weight of the amino acids loaded on the resin for solid-phase synthesis. The yield for the isolation of the amino acids loaded on the resin for solid-phase synthesis was calculated based on the weight of amino acids used in the loading step and the weight of amino acids recovered in the above operation.

Yield for amino acid isolation: Calculated by subtracting the residual amount of the solvent (such as DCM, TFA, or DMF) used in the reaction or isolation operation from the dry weight of the amino acids obtained. The residual solvent was measured under the NMR conditions 1 or 2 and calculated by the method shown below.

Residual amount of DCM: 5 mg of cleaved amino acids was weighed precisely and dissolved in 700 μL of DMSO-$d_6$ to prepare a sample, and then $^1$H-NMR was measured. Using the aromatic ring region originating from the Fmoc group (δ:7.90-7.29, 8H, m) as a standard, the residual amount of solvent contained in the amino acids was calculated from the integral ratio of DCM (δ:5.76, 2H, s) using the following formula.

Weight % of residual DCM to amino acids=((84.93 (DCM molecular weight))×(integral ratio of DCM when integral value of aromatic ring region of amino acid is 1))×100/((84.93 (DCM molecular weight))×(integral ratio of DCM when integral value of aromatic ring region of amino acid is 1)+(molecular weight of amino acid))

Residual amount of DMF: 5 mg of cleaved amino acids was weighed precisely and dissolved in 700 μL of DMSO-$d_6$ to prepare a sample, and then $^1$H-NMR was measured. Using the aromatic ring region originating from the Fmoc group (δ: 7.90-7.29, 8H, m) as a standard, the residual amount of solvent contained in the amino acids was calculated from the integral ratio of DMF (δ:7.95, 1 H, s) using the following formula.

Weight % of residual DMF to amino acids=((73.09 (DMF molecular weight))×(integral ratio of DMF when integral value of aromatic ring region of amino acid is 1))×100/((73.09 (DMF molecular weight))×(integral ratio of DMF when integral value of aromatic ring region of amino acid is 1)+(molecular weight of amino acid))

Residual amount of TFA: 5 mg of cleaved amino acids and 5 mg of an internal standard substance were weighed precisely and dissolved in 700 μL of DMSO-$d_6$ to prepare a sample, and then $^{19}$F-NMR was measured using the internal standard substance (δ: −76.0, 6F, s) as a standard, and the residual amount of solvent contained in the amino acids was calculated from the integral ratio of TFA (δ:−89.4, 3F, s) using the following formula.

Weight % of residual TFA contained in amino acids=((weight of internal standard substance)×(114.02(molecular weight of TFA))×(6(number of fluorine atoms in internal standard substance))×(integral value of TFA)×100)/((weight of amino acids)×(258.12 (molecular weight of internal standard substance))×(3(number of fluorine atoms in TFA))×(integral value of internal standard substance))

[Measurement Method]

The measurement conditions by HPLC are shown below.

[High-Performance Liquid Chromatography Conditions 1]

Apparatus: Acquity UPLC/H-class, Acquity QDa manufactured by Waters

Column: Ascentis Express $C_{18}$ (2.1 mm I.D.×50 mm)

Mobile phase: Water containing 0.05% trifluoroacetic acid (A) and acetonitrile containing 0.05% trifluoroacetic acid (B)

Elution: stepwise solvent gradient elution from 5% B to 100% B (4.0 min), then holding at 100% B (0.5 min)

Flow rate: 1.0 mL/min

Column temperature: 35° C.

[High-Performance Liquid Chromatography Conditions 2]

Apparatus: Acquity UPLC/H-class manufactured by Waters

Column: capcell core adme (3.0 mm I.D.×150 mm)

Mobile phase: Water containing 0.05% trifluoroacetic acid (A) and acetonitrile containing 0.05% trifluoroacetic acid (B)

Elution: stepwise solvent gradient elution from 30% B to 70% B (20.0 min), then holding at 100% B (2.0 min)
Flow rate: 0.3 mL/min
Column temperature: 30° C.
[High-Performance Liquid Chromatography Conditions 3]
Apparatus: Acquity UPLC/H-class manufactured by Waters
Column: CSH Fluoro-phenyl (2.1 mm I.D.×150 mm)
Mobile phase: Water containing 0.1% formic acid (A) and acetonitrile containing 0.1% formic acid (B)
Elution: stepwise solvent gradient elution from 5% B to 100% B (15.0 min), then holding at 100% B (3.0 min), 5% B (0.01 min) and 5% B (2 min)
Flow rate: 0.3 mL/min
Column temperature: 35° C.
[HPLC Retention Time for Amino Acids]

TABLE 1

| Amino Acid Name | Exact MS | Measurement Conditions | Retention Time (min) | m/z |
|---|---|---|---|---|
| Fmoc-MeAsp (OH)-pip | 436.20 | Conditions 1 | 2.179 | 437.26 [M + H]+ |
| | | Conditions 2 | 15.673 | n/a |
| Fmoc-Asp (OH)-pip | 422.18 | Conditions 1 | 2.076 | 423.12 [M + H]+ |
| Fmoc-MeAsp (OH)-pyrro | 422.18 | Conditions 1 | 1.971 | 423.41 [M + H]+ |
| | | Conditions 2 | 13.033 | n/a |
| Fmoc-MeAsp (OH)-NMe2 | 396.17 | Conditions 1 | 1.888 | 397.08 [M + H]+ |
| | | Conditions 3 | 9.480 | n/a |
| Fmoc-MeAsp (O-tBu)-pip | 492.26 | Conditions 1 | 3.158 | 493.41 [M + H]+ |
| Fmoc-Asp (O-tBu)-pip | 478.25 | Conditions 1 | 2.778 | 479.39 [M + H]+ |

n/a: Not available

The measurement conditions by NMR are shown below.
[NMR Conditions 1]

The $^{1}$H-NMR spectrum was measured using a JEOL 500 MHz Royal HFX probe, the chemical shift of $Me_4Si$ used as the internal standard substance was set at 0 ppm, and a deuterium lock signal from a sample solvent was consulted. The chemical shift of a signal from a compound to be analyzed was expressed in ppm. Abbreviations for splitting of a signal were expressed as s=singlet and m=multiplet. The integral value of signals was calculated on the basis of a ratio of the signal area intensity of each signal.
[NMR Conditions 2]

The $^{19}$F-NMR spectrum was measured using a JEOL 500 MHz Royal HFX probe, the chemical shift of 3,5-bis(trifluoromethyl)benzoic acid (GC purity: 99.3%) used as the internal standard substance was set at −76 ppm, and the chemical shift of a signal from a compound to be analyzed was expressed in ppm. Abbreviations for splitting of a signal were expressed as s=singlet. The integral value of signals was calculated on the basis of a ratio of the signal area intensity of each signal.

Example of Description of Loading Reaction on Resin for Solid-Phase Synthesis In the present specification, if the compound is bound to a polymer or resin, the polymer or resin portion may be expressed as a circle (○). For the purpose of clarifying the point of reaction on the resin portion, the chemical structure of the reaction site may be expressed by connecting it to the circle (○). For example, in the following structure Fmoc-MeAsp(O-CTC)-pip, the 2-chlorotrityl group of the resin (CTC resin) is bound to the side-chain carboxyl group of Asp via an ester bond. pip means a piperidinyl group, and in the above structure, the C-terminus carboxyl group forms an amide bond with piperidine.

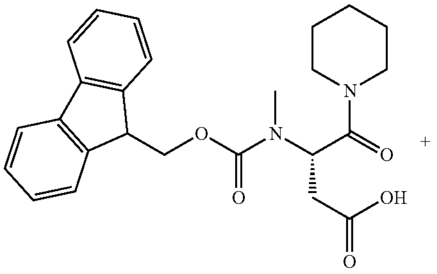

Fmoc-MeAsp(OH)-pip

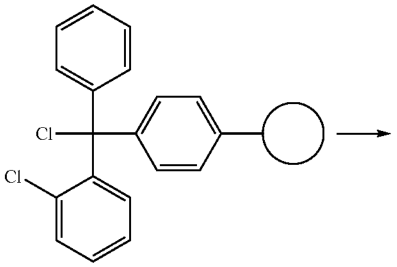

CTC resin

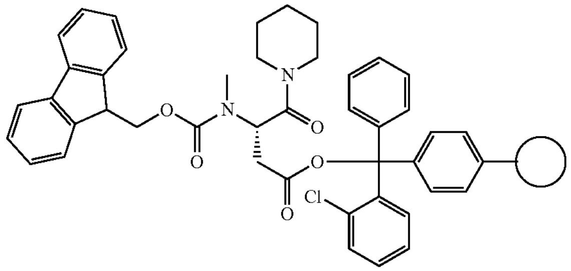

Fmoc-MeAsp(O-CTC)-pip

The 2-chlorotrityl chloride resin (1.00 to 1.37 mmol/g, 100-200 mesh, 1% DVB) was purchased from Sunresin New Materials Co., Ltd (Xi'an, China). Fmoc-MeAsp(O-tBu)-OH was purchased from New England Chemicals (New York, USA), GL Biochem (Shanghai, China), ChemBioBank (Shanghai, China), and SINO High Goal Chemical Technology Co., Ltd. (Shanghai, China). Among the reaction solvents used in the solid-phase synthesis reaction, dichloromethane, methanol, t-butyl methyl ether, and cyclopentyl methyl ether of dehydrated grade were purchased from FUJIFILM Wako Pure Chemical Corporation. Piperidine and diisopropylethylamine were purchased from Watanabe Chemical Co., Ltd. N, N-dimethylformamide of dehydrated grade was purchased from FUJIFILM Wako Pure Chemical Corporation, Junsei Chemical Co., Ltd. or Mitsubishi Gas Chemical Company, Inc. 2-Methyltetrahydrofuran was purchased from FUJIFILM Wako Pure Chemical Corporation and Watanabe Chemical Co., Ltd.

A constant-temperature shaker (Model MMS-1 manufactured by EYELA) was used during solid-phase synthesis.

The resin for solid-phase synthesis was dried by vacuum pump at 25° C. for 12 hours or more at 5 torr or less. It was considered a constant weight when the weight change of two consecutive weight measurements of the resin was within 1% of the weight of the resin.

Example 1: Reaction of Loading Fmoc-MeAsp(OH)-pip on CTC Resin

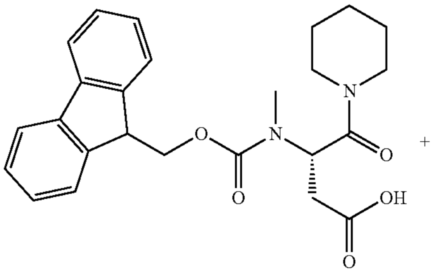

Fmoc-MeAsp(OH)-pip

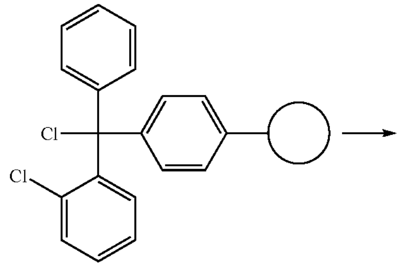

CTC resin

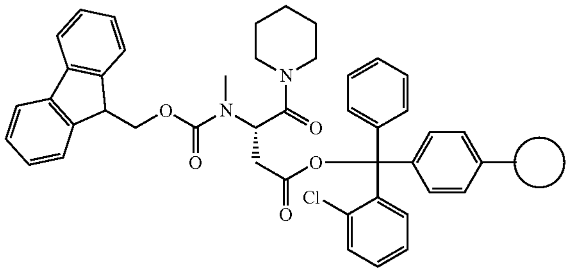

Fmoc-MeAsp(O-CTC)-pip

Example 1-1-1: CTC Resin is Swollen with DCM and Loading Reaction is Performed in MeTHF 1.36 mmol/g of CTC resin (146.9 mg, 0.196 mmol) was placed in a column for solid-phase synthesis, to which DCM (1.2 mL) was added and the mixture was shaken for 30 minutes to swell the CTC resin. After filtration, a MeTHF solution (1.2 mL) of Fmoc-MeAsp(OH)-pip (50.87 mg, 0.117 mmol) and DIPEA (56 μL, 0.321 mmol) was added to the CTC resin and the mixture was shaken for 23 hours at room temperature. The reaction conversion ratio was 90%. After filtration, a DMF mixed solution (DMF:methanol:DIPEA=85:10:5 (total: 1.2 mL)) was added to the CTC resin and the mixture was shaken for 2 hours at room temperature. After filtration, the CTC resin was washed four times with DMF (1.5 mL) and four times with methanol (1.5 mL), then the CTC resin was dried by vacuum pump to obtain Fmoc-MeAsp(O-CTC)-pip (180.0 mg). The yield by the Fmoc quantitation method was 97%.

Example 1-1-2: CTC Resin is Swollen with DCM and Loading Reaction is Performed in Mixed Solvent of MeTHF:DCM=1:1

1.36 mmol/g of CTC resin (286.4 mg, 0.389 mmol) was placed in a column for solid-phase synthesis, to which DCM (2.3 mL) was added and the mixture was shaken for 30 minutes to swell the CTC resin. DCM was filtered and discharged. A separately prepared amino acid solution of Fmoc-MeAsp(OH)-pip (100.2 mg, 0.229 mmol), DIPEA (114 μL, 0.641 mmol), MeTHF (1.2 mL) and DCM (1.2 mL) was added to the CTC resin and the mixture was shaken for 21 hours at room temperature. The reaction conversion ratio was 99%. After filtration, a DMF mixed solution (DMF:methanol:DIPEA=85:10:5 (total: 2.3 mL)) was added to the CTC resin and the mixture was shaken for 2 hours at room temperature. After filtration, the CTC resin was washed four times with DMF (2.9 mL) and four times with methanol (2.9 mL), then the CTC resin was dried by vacuum pump to obtain Fmoc-MeAsp(O-CTC)-pip (363.5 mg). The yield by the Fmoc quantitation method was 100%.

Example 1-1-3: CTC Resin is Swollen with DCM and Loading Reaction is Performed in Mixed Solvent of MeTHF:DCM=1:2

1.36 mmol/g of CTC resin (145.77 mg, 0.198 mmol) was placed in a column for solid-phase synthesis, to which DCM (1.2 mL) was added and the mixture was shaken for 30 minutes to swell the CTC resin. DCM was filtered and discharged. A separately prepared amino acid solution of Fmoc-MeAsp(OH)-pip (50.66 mg, 0.116 mmol), DIPEA (56 μL, 0.321 mmol), MeTHF (0.4 mL) and DCM (0.8 mL) was added to the CTC resin and the mixture was shaken for 6 hours at room temperature. The reaction conversion ratio was 100%. After filtration, a DMF mixed solution (DMF:methanol:DIPEA=85:10:5 (total: 1.2 mL)) was added to the CTC resin and the mixture was shaken for 2 hours at room temperature. After filtration, the CTC resin was washed four times with DMF (1.5 mL) and four times with methanol (1.5 mL), then the CTC resin was dried by vacuum pump to obtain Fmoc-MeAsp(O-CTC)-pip (181.1 mg). The yield by the Fmoc quantitation method was 96%.

Example 1-1-3-2: Experiment from the Deprotection Reaction of Fmoc-MeAsp(O-tBu)-pip Through the Loading Step. CTC Resin is Swollen With DCM and Loading Reaction is Performed in Mixed Solvent of MeTHF:DCM=1:2

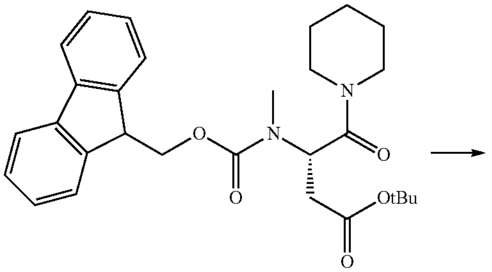

Fmoc-MeAsp(O—tBu)-pip

-continued

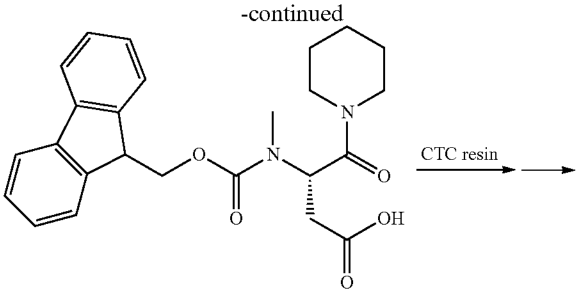

Fmoc-MeAsp(OH)-pip

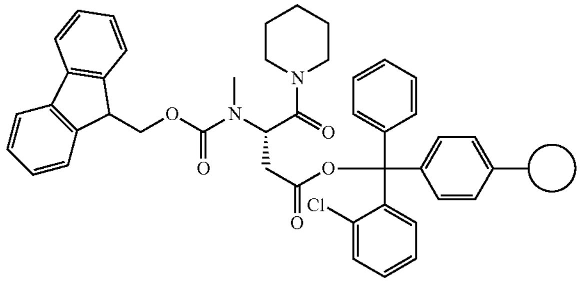

Fmoc-MeAsp(O-CTC)-pip

Fmoc-MeAsp(O-tBu)-pip (8.012 g, 16.24 mmol) was dissolved in MeTHF (40.0 mL). To the solution was added HMDS (4.1 mL, 19.5 mmol) at 0° C., then TMSOTf(3.2 mL, 17.9 mmol) was added dropwise. The reaction solution was heated to 25° C., then stirred for 2 hours. At 0° C., a 5% sodium carbonate solution (80 mL) was added to the reaction solution, which was heated to 25° C., and then stirred for 1 hour. After a back-extraction using MTBE (40 mL), the aqueous layer was washed with MTBE (80 mL). MeTHF (40 mL) was added to the aqueous layer, followed by phosphoric acid (5.6 mL, 81 mmol). After discharging the aqueous layer, the organic layer was washed three times with a 15% sodium chloride solution (40 mL). $MgSO_4$ (6.01 g, 0.75 w/w) was added to the obtained MeTHF solution, which was then stirred for 30 minutes. $MgSO_4$ was removed by filtration and washed with MeTHF (16 mL). Of the 38.7114 g of MeTHF solution of Fmoc-MeAsp(OH)-pip obtained, 37.2225 g was used to proceed to the next step.

1.00 mmol/g of CTC resin (17.18 g, 17.18 mmol) was placed in a column for solid-phase synthesis, to which DCM (172 mL) was added and the mixture was shaken for 30 minutes to swell the CTC resin. After filtration, to the CTC resin, MeTHF (10 mL) was further added to the MeTHF solution (containing 36 mL of MeTHF) containing Fmoc-MeAsp(OH)-pip (6.24 g, 14.30 mmol) obtained above, DIPEA (6.70 mL, 38.5 mmol) and DCM (92 mL) were added, and the mixture was shaken for 18 hours at room temperature. The reaction conversion ratio was 100%. After filtration, a DMF mixed solution (DMF:methanol:DIPEA=85:10:5 (total: 137.4 mL)) was added to the CTC resin and the mixture was shaken for 2 hours at room temperature. After filtration, the CTC resin was washed four times with DMF (92 mL) and four times with methanol (172 mL), then the CTC resin was dried by vacuum pump to obtain Fmoc-MeAsp(O-CTC)-pip (23.1879 g). The yield by the Fmoc quantitation method was 97%. The obtained Fmoc-MeAsp(O-CTC)-pip (1.0099 g) was placed in a column for solid-phase synthesis, to which DMF (8 mL) was added, and then the column was shaken for 30 minutes. After filtration, the CTC resin was washed four times with DCM (8 mL). A 1% TFA-DCM solution (8 mL) was added and the mixture was shaken for 1 minute to cleave the amino acids from the resin. After filtration, the filtrate was set aside. A 1% TFA-DCM solution was added again to the resin, which was shaken for 1 minute, and the filtrate was collected after filtration (this operation was repeated three times). The CTC resin was further washed with DCM (8 mL) twice. All the filtrates and the washing liquids were mixed and concentrated under reduced pressure. The concentrated residue was dried by vacuum pump to obtain 485.4 mg of Fmoc-MeAsp(OH)-pip. The yield by the isolation method was 91%.

Example 1-1-3-3: Experiment From the Deprotection Reaction of Fmoc-MeAsp(O-tBu)-pip Through the Loading Step. Use of DCM as the Extraction Solvent After the Deprotection Reaction, CTC Resin is Swollen With DCM and Loading Reaction is Performed With DCM Fmoc-MeAsp(O-tBu)-pip (8.00 g, 16.24 mmol) was dissolved in MeTHF (40.0 mL). To the solution was added HMDS (4.1 mL, 19.5 mmol) at 0° C., then TMSOTf(3.2 mL, 17.9 mmol) was added dropwise. The reaction solution was heated to 25° C., then stirred for 2 hours. At 0° C., a 5% sodium carbonate solution (80 mL) was added dropwise to the reaction solution, which was heated to 25° C., and then stirred for 1 hour. After a back-extraction using MTBE (40 mL), the aqueous layer was washed with MTBE (80 mL). DCM (40 mL) was added to the aqueous layer, followed by phosphoric acid (5.6 mL, 81 mmol). After discharging the aqueous layer, the organic layer was washed three times with a 15% sodium chloride solution (40 mL). $MgSO_4$ (4.99 g, 0.63 w/w) was added to the obtained DCM solution, which was then stirred for 30 minutes. $MgSO_4$ was removed by filtration and washed with DCM (16 mL). Of the 42.6802 g of DCM solution (containing 27.6 mL of DCM) of Fmoc-MeAsp(OH)-pip obtained, 41.1315 g was used to proceed to the next step.

1.36 mmol/g of CTC resin (17.19 g, 23.37 mmol) was placed in a column for solid-phase synthesis, to which DCM (137 mL) was added and the mixture was shaken for 30 minutes to swell the CTC resin. After filtration, the DCM solution containing Fmoc-MeAsp(OH)-pip (5.98 g, 13.74 mmol) obtained above, DIPEA (6.70 mL, 38.5 mmol), and DCM (96 mL) were added to the CTC resin and the mixture was shaken for 3 hours at room temperature. The reaction conversion ratio was 99.8%. After filtration, a DMF mixed solution (DMF:methanol:DIPEA=85:10:5 (total: 137.4 mL)) was added to the CTC resin and the mixture was shaken for 2 hours at room temperature. After filtration, the CTC resin was washed four times with DMF (172 mL) and four times with methanol (172 mL), then the CTC resin was dried by vacuum pump to obtain Fmoc-MeAsp(O-CTC)-pip (24.1879 g). The yield by the Fmoc quantitation method was 89%. The obtained Fmoc-MeAsp(O-CTC)-pip (2.0023 g) was placed in a column for solid-phase synthesis, to which DMF (16 mL) was added, and then the column was shaken for 30 minutes. After filtration, the CTC resin was washed four times with DCM (16 mL). A 1% TFA-DCM solution (8 mL) was added and the mixture was shaken for 1 minute to cleave the amino acids from the resin. After filtration, the filtrate was set aside. A 1% TFA-DCM solution was added again to the resin, which was shaken for 1 minute, and the filtrate was collected after filtration (this operation was repeated four times). The CTC resin was further washed with DCM (16 mL) twice. All the filtrates and the washing liquids were mixed and concentrated under reduced pressure. The concentrated residue was dried by vacuum pump to obtain 967.9 mg of Fmoc-MeAsp(OH)-pip. The yield by the isolation method was 80%.

Example 1-1-3-4: Experiment From the Deprotection Reaction of Fmoc-MeAsp(O-tBu)-Pip Through the Loading Step. In the Deprotection Step. Loading Reaction is Performed without Removal of Water by Desiccant. CTC Resin is Swollen With DCM and Loading Reaction is Performed in Mixed Solvent of MeTHF:DCM=1:2

Fmoc-MeAsp(O-tBu)-pip (13.19 g, 26.8 mmol) was dissolved in MeTHF (56.0 mL). To the solution was added HMDS (5.7 mL, 27.3 mmol) at 0° C., then TMSOTf(4.5 mL, 25.0 mmol) was added dropwise. The reaction solution was heated to 25° C., then stirred for 1 hour and 30 minutes. At 0° C., a 5% sodium carbonate solution (132 mL) was added to the reaction solution, which was heated to 25° C., and then stirred for 2 hours. After a back-extraction using MTBE (66 mL), the aqueous layer was washed with MTBE (132 mL). MeTHF (66 mL) was added to the aqueous layer, followed by phosphoric acid (9.2 mL, 134 mmol). After discharging the aqueous layer, the organic layer was washed twice with a 15% sodium chloride solution (66 mL). Of the 76.72 g of MeTHF solution (containing 76.1 mL of MeTHF) of Fmoc-MeAsp(OH)-pip obtained, 39.37 g was used to proceed to the next step.

1.36 mmol/g of CTC resin (17.2 g, 23.39 mmol) was placed in a column for solid-phase synthesis, to which DCM (137 mL) was added and the mixture was shaken for 30 minutes to swell the CTC resin. After filtration, to the CTC resin, MeTHF (7.0 mL) was further added to the MeTHF solution (containing 39.0 mL) containing Fmoc-MeAsp (OH)-pip (6.00 g, 13.74 mmol) obtained above, DIPEA (6.70 mL, 38.5 mmol) and DCM (92 mL) were added, and the mixture was shaken for 2 hours at room temperature. The reaction conversion ratio was 99.7%. After filtration, a DMF mixed solution (DMF:methanol:DIPEA=85:10:5 (total: 137.4 mL)) was added to the CTC resin and the mixture was shaken for 2 hours at room temperature. After filtration, the CTC resin was washed four times with DMF (172 mL) and four times with methanol (172 mL), then the CTC resin was dried by vacuum pump to obtain Fmoc-MeAsp(O-CTC)-pip (21.88 g). The yield by the Fmoc quantitation method was 94%. The obtained Fmoc-MeAsp(O-CTC)-pip (0.9996 g) was placed in a column for solid-phase synthesis, to which DMF (8 mL) was added, and then the column was shaken for 30 minutes. After filtration, the CTC resin was washed four times with DCM (8 mL). A 1% TFA-DCM solution (8 mL) was added and the mixture was shaken for 1 minute to cleave the amino acids from the resin. After filtration, the filtrate was set aside. A 1% TFA-DCM solution was added again to the resin, which was shaken for 1 minute, and the filtrate was collected after filtration (this operation was repeated three times). The CTC resin was further washed with DCM (8 mL) twice. All the filtrates and the washing liquids were mixed and concentrated under reduced pressure. The concentrated residue was dried by vacuum pump to obtain 449.4 mg of Fmoc-MeAsp(OH)-pip. The yield by the isolation method was 91%.

Example 1-1-4: CTC Resin is Swollen with DCM and Loading Reaction is Performed in Mixed Solvent of MeTHF:DCM=1:10

1.36 mmol/g of CTC resin (145.39 mg, 0.198 mmol) was placed in a column for solid-phase synthesis, to which DCM (1.2 mL) was added and the mixture was shaken for 30 minutes to swell the CTC resin. DCM was filtered and discharged. A separately prepared amino acid solution of Fmoc-MeAsp(OH)-pip (50.48 mg, 0.116 mmol), DIPEA (56 μL, 0.321 mmol), MeTHF (0.1 mL) and DCM (1.0 mL) was added to the CTC resin and the mixture was shaken for 6 hours at room temperature. The reaction conversion ratio was 100%. After filtration, a DMF mixed solution (DMF:methanol:DIPEA=85:10:5 (total: 1.2 mL)) was added to the CTC resin and the mixture was shaken for 2 hours at rom temperature. After filtration, the CTC resin was washed four times with DMF (1.5 mL) and four times with methanol (1.5 mL), then the CTC resin was dried by vacuum pump to obtain Fmoc-MeAsp(O-CTC)-pip (178.1 mg). The yield by the Fmoc quantitation method was 85%.

Example 1-2-1: CTC Resin is Swollen with DCM and Loading Reaction is Performed in MTBE 1.36 mmol/g of CTC resin (287.1 mg, 0.390 mmol) was placed in a column for solid-phase synthesis, to which DCM (2.3 mL) was added and the mixture was shaken for 30 minutes to swell the CTC resin. After filtration, an MTBE solution (2.3 mL) of Fmoc-MeAsp(OH)-pip (100.7 mg, 0.231 mmol) and DIPEA (114 μL, 0.641 mmol) was added to the CTC resin and the mixture was shaken for 15 hours at room temperature. The reaction conversion ratio was 76%. After filtration, a DMF mixed solution (DMF:methanol:DIPEA=85:10:5 (total: 2.3 mL)) was added to the CTC resin and the mixture was shaken for 2 hours at room temperature. After filtration, the CTC resin was washed four times with DMF (2.9 mL) and four times with methanol (2.9 mL), then the CTC resin was dried by vacuum pump to obtain Fmoc-MeAsp(O-CTC)-pip (363.7 mg). The yield by the Fmoc quantitation method was 79%.

Example 1-2-2: CTC Resin is Swollen with DCM and Loading Reaction is Performed in Mixed Solvent of MTBE:DCM=1:1

1.36 mmol/g of CTC resin (286.6 mg, 0.390 mmol) was placed in a column for solid-phase synthesis, to which DCM (2.3 mL) was added and the mixture was shaken for 30 minutes to swell the CTC resin. DCM was filtered and discharged. A separately prepared amino acid solution of Fmoc-MeAsp(OH)-pip (100.1 mg, 0.229 mmol), DIPEA (114 μL, 0.641 mmol), MTBE (1.2 mL) and DCM (1.2 mL) was added to the CTC resin and the mixture was shaken for 17 hours at room temperature. The reaction conversion ratio was 100%. After filtration, a DMF mixed solution (DMF:methanol:DIPEA=85:10:5 (total: 2.3 mL)) was added to the CTC resin and the mixture was shaken for 2 hours at room temperature. After filtration, the CTC resin was washed four times with DMF (2.9 mL) and four times with methanol (2.9 mL), then the CTC resin was dried by vacuum pump to obtain Fmoc-MeAsp(O-CTC)-pip (355.9 mg). The yield by the Fmoc quantitation method was 90%.

Example 1-2-3: CTC Resin is Swollen with DCM and Loading Reaction is Performed in Mixed Solvent of MTBE:DCM=1:2

1.36 mmol/g of CTC resin (148.38 mg, 0.202 mmol) was placed in a column for solid-phase synthesis, to which DCM (1.2 mL) was added and the mixture was shaken for 30 minutes to swell the CTC resin. DCM was filtered and discharged. A separately prepared amino acid solution of Fmoc-MeAsp(OH)-pip (51.71 mg, 0.118 mmol), DIPEA (56 μL, 0.321 mmol), MTBE solution (0.4 mL) and DCM (0.8 mL) was added to the CTC resin and the mixture was shaken for 18 hours at room temperature. The reaction conversion ratio was 100%. After filtration, a DMF mixed solution (DMF:methanol:DIPEA=85:10:5 (total: 1.2 mL)) was added to the CTC resin and the mixture was shaken for 2 hours at room temperature. After filtration, the CTC resin was washed four times with DMF (1.5 mL) and four times with methanol (1.5 mL), then the CTC resin was dried by vacuum pump to obtain Fmoc-MeAsp(O-CTC)-pip (186.2 mg). The yield by the Fmoc quantitation method was 73%.

Example 1-2-4: CTC Resin is Swollen with DCM and Loading Reaction is Performed in Mixed Solvent of MTBE:DCM=1:10

1.36 mmol/g of CTC resin (143.72 mg, 0.195 mmol) was placed in a column for solid-phase synthesis, to which DCM (1.2 mL) was added and the mixture was shaken for 30 minutes to swell the CTC resin. DCM was filtered and discharged. A separately prepared amino acid solution of Fmoc-MeAsp(OH)-pip (50.24 mg, 0.115 mmol), DIPEA (56 μL, 0.321 mmol), MTBE (0.1 mL) and DCM (1.0 mL) was added to the CTC resin and the mixture was shaken for 6 hours at room temperature. The reaction conversion ratio was 100%. After filtration, a DMF mixed solution (DMF:methanol:DIPEA=85:10:5 (total: 1.2 mL)) was added to the CTC resin and the mixture was shaken for 2 hours at room temperature. After filtration, the CTC resin was washed four times with DMF (1.5 mL) and four times with methanol (1.5 mL), then the CTC resin was dried by vacuum pump to obtain Fmoc-MeAsp(O-CTC)-pip (174.9 mg). The yield by the Fmoc quantitation method was 88%.

Example 1-3-1: CTC Resin is Swollen with DCM and Loading Reaction is Performed with CPME 1.36 mmol/g of CTC resin (286.8 mg, 0.390 mmol) was placed in a column for solid-phase synthesis, to which DCM (2.3 mL) was added and the mixture was shaken for 30 minutes to swell the CTC resin. After filtration, a CPME solution (2.3 mL) of Fmoc-MeAsp(OH)-pip (100.0 mg, 0.229 mmol) and DIPEA (114 μL, 0.641 mmol) was added to the CTC resin and the mixture was shaken for 17 hours at room temperature. The reaction conversion ratio was 39%. After filtration, a DMF mixed solution (DMF:methanol:DIPEA=85:10:5 (total: 2.3 mL)) was added to the CTC resin and the mixture was shaken for 2 hours at room temperature. After filtration, the CTC resin was washed four times with DMF (2.9 mL) and four times with methanol (2.9 mL), then the CTC resin was dried by vacuum pump to obtain Fmoc-MeAsp(O-CTC)-pip (353.2 mg). The yield by the Fmoc quantitation method was 72%.

Example 1-3-2: CTC Resin is Swollen with DCM and Loading Reaction is Performed in Mixed Solvent of CPME:DCM=1:1

1.36 mmol/g of CTC resin (287.1 mg, 0.390 mmol) was placed in a column for solid-phase synthesis, to which DCM (2.3 mL) was added and the mixture was shaken for 30 minutes to swell the CTC resin. DCM was filtered and discharged. A separately prepared mixed solution of Fmoc-MeAsp(OH)-pip (100.6 mg, 0.230 mmol), DIPEA (112 μL, 0.641 mmol), CPME (1.15 mL) and DCM (1.15 mL) was added to the CTC resin and the mixture was shaken for 3 hours at room temperature. The reaction conversion ratio was 99%. After filtration, a DMF mixed solution (DMF:methanol:DIPEA=85:10:5 (total: 2.3 mL)) was added to the CTC resin and the mixture was shaken for 2 hours at room temperature. After filtration, the CTC resin was washed four times with DMF (2.9 mL) and four times with methanol (2.9 mL), then the CTC resin was dried by vacuum pump to obtain Fmoc-MeAsp(O-CTC)-pip (366.8 mg). The yield by the Fmoc quantitation method was 77%.

Example 1-3-3: CTC Resin is Swollen with DCM and Loading Reaction is Performed in Mixed Solvent of CPME:DCM=1:2

1.36 mmol/g of CTC resin (144.00 mg, 0.196 mmol) was placed in a column for solid-phase synthesis, to which DCM (1.2 mL) was added and the mixture was shaken for 30 minutes to swell the CTC resin. DCM was filtered and discharged. A separately prepared mixed solution of Fmoc-MeAsp(OH)-pip (50.23 mg, 0.115 mmol), DIPEA (56 μL, 0.321 mmol), CPME (0.4 mL) and DCM (0.8 mL) was added to the CTC resin and the mixture was shaken for 18 hours at room temperature. The reaction conversion ratio was 100%. After filtration, a DMF mixed solution (DMF:methanol:DIPEA=85:10:5 (total: 1.2 mL)) was added to the CTC resin and the mixture was shaken for 2 hours at room temperature. After filtration, the CTC resin was washed four times with DMF (1.5 mL) and four times with methanol (1.5 mL), then the CTC resin was dried by vacuum pump to obtain Fmoc-MeAsp(O-CTC)-pip (182.0 mg). The yield by the Fmoc quantitation method was 79%.

Example 1-3-4: CTC Resin is Swollen with DCM and Loading Reaction is Performed in Mixed Solvent of CPME:DCM=1:10

1.36 mmol/g of CTC resin (144.45 mg, 0.196 mmol) was placed in a column for solid-phase synthesis, to which DCM (1.2 mL) was added and the mixture was shaken for 30 minutes to swell the CTC resin. DCM was filtered and discharged. A separately prepared mixed solution of Fmoc-MeAsp(OH)-pip (50.07 mg, 0.115 mmol), DIPEA (56 μL, 0.321 mmol), CPME (0.1 mL) and DCM (1.0 mL) was added to the CTC resin and the mixture was shaken for 6 hours at room temperature. The reaction conversion ratio was 100%. After filtration, a DMF mixed solution (DMF:methanol:DIPEA=85:10:5 (total: 1.2 mL)) was added to the CTC resin and the mixture was shaken for 2 hours at room temperature. After filtration, the CTC resin was washed four times with DMF (1.5 mL) and four times with methanol (1.5 mL), then the CTC resin was dried by vacuum pump to obtain Fmoc-MeAsp(O-CTC)-pip (175.7 mg). The yield by the Fmoc quantitation method was 84%.

Example 1-4-1: CTC Resin is Swollen with DCM and Loading Reaction is Performed in DCM 1.36 mmol/g of CTC resin (287.1 mg, 0.390 mmol) was placed in a column for solid-phase synthesis, to which DCM (2.3 mL) was added and the mixture was shaken for 30 minutes to swell the CTC resin. After filtration, a DCM solution (2.3 mL) of Fmoc-MeAsp(OH)-pip (99.83 mg, 0.229 mmol) and DIPEA (114 μL, 0.641 mmol) was added to the CTC resin and the mixture was shaken for 3 hours at room temperature. The reaction conversion ratio was 100%. After filtration, a DMF mixed solution (DMF:methanol:DIPEA=85:10:5 (total: 2.3 mL)) was added to the CTC resin and the mixture was shaken for 2 hours at room temperature. After filtration, the CTC resin was washed four times with DMF (2.9 mL) and four times with methanol (2.9 mL), then the CTC resin was dried by vacuum pump to obtain Fmoc-MeAsp(O-CTC)-pip (375.2 mg). The yield by the Fmoc quantitation method was 97%.

Example 1-5-1: CTC Resin is Swollen with MeTHF and Loading Reaction is Performed in MeTHF 1.36 mmol/g of CTC resin (146.9 mg, 0.200 mmol) was placed in a column for solid-phase synthesis, to which MeTHF (1.2 mL) was added and the mixture was shaken for 30 minutes to swell the CTC resin. After filtration, a MeTHF solution (1.2 mL) of Fmoc-MeAsp(OH)-pip (50.56 mg, 0.116 mmol) and DIPEA (56 μL, 0.321 mmol) was added to the CTC resin and the mixture was shaken for 18 hours at room temperature. The reaction conversion ratio was 33%. After filtration, a DMF mixed solution (DMF:methanol: DIPEA=85:10:5 (total: 1.5 mL)) was added to the CTC resin and the mixture was shaken for 2 hours at room temperature. After filtration, the CTC resin was washed four times with DMF (1.5 mL) and four times with methanol (1.5 mL), then the CTC resin was dried by vacuum pump to obtain Fmoc-MeAsp(O-CTC)-pip (180.0 mg). The yield by the Fmoc quantitation method was 49%.

Example 1-6-1: CTC Resin is Swollen with CPME and Loading Reaction is Performed in CPME 1.36 mmol/g of CTC resin (286.0 mg, 0.389 mmol) was placed in a column for solid-phase synthesis, to which CPME (2.3 mL) was added and the mixture was shaken for 30 minutes to swell the CTC resin. After filtration, a CPME solution (2.3 mL) of Fmoc-MeAsp(OH)-pip (99.6 mg, 0.228 mmol) and DIPEA (114 μL, 0.641 mmol) was added to the CTC resin and the mixture was shaken for 23 hours at room temperature. The reaction conversion ratio was 67%. After filtration, a DMF mixed solution (DMF:methanol: DIPEA=85:10:5 (total: 2.3 mL)) was added to the CTC resin and the mixture was shaken for 2 hours at room temperature. After filtration, the CTC resin was washed four times with DMF (2.9 mL) and four times with methanol (2.9 mL), then the CTC resin was dried by vacuum pump to obtain Fmoc-MeAsp(O-CTC)-pip (349.8 mg). The yield by the Fmoc quantitation method was 51%.

Example 2: Reaction of Loading Fmoc-Asp(OH)-pip on CTC Resin

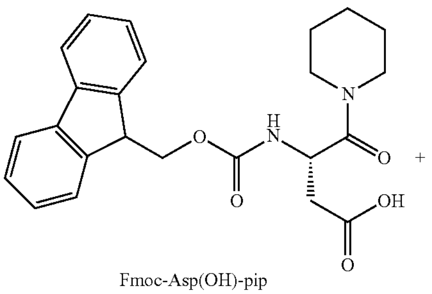

Fmoc-Asp(OH)-pip

-continued

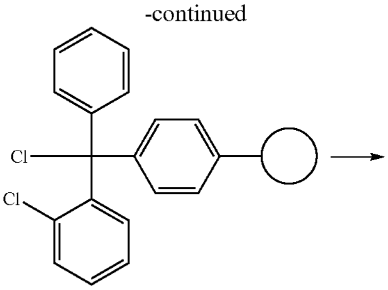

CTC resin

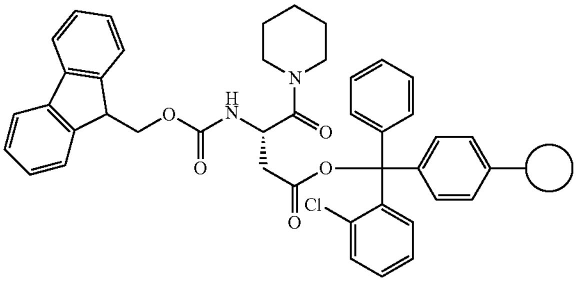

Fmoc-Asp(O-CTC)-pip

Example 2-1-1: CTC Resin is Swollen with DCM and Loading Reaction is Performed with MeTHF 1.36 mmol/g of CTC resin (148.56 mg, 0.202 mmol) was placed in a column for solid-phase synthesis, to which DCM (1.2 mL) was added and the mixture was shaken for 30 minutes to swell the CTC resin. After filtration, a MeTHF solution (1.2 mL) of Fmoc-Asp(OH)-pip (50.33 mg, 0.119 mmol) and DIPEA (58 μL, 0.331 mmol) was added to the CTC resin and the mixture was shaken for 18 hours at room temperature. The reaction conversion ratio was 92%. After filtration, a DMF mixed solution (DMF:methanol: DIPEA=85:10:5 (total: 2.3 mL)) was added to the CTC resin and the mixture was shaken for 2 hours at room temperature. After filtration, the CTC resin was washed four times with DMF (1.5 mL) and four times with methanol (1.5 mL), then the CTC resin was dried by vacuum pump to obtain Fmoc-Asp(O-CTC)-pip (194.1 mg). The yield by the Fmoc quantitation method was 84%.

Example 2-1-2: CTC Resin is Swollen with DCM and Loading Reaction is Performed in Mixed Solvent of MeTHF:DCM=1:1

1.36 mmol/g of CTC resin (147.7 mg, 0.201 mmol) was placed in a column for solid-phase synthesis, to which DCM (2.3 mL) was added and the mixture was shaken for 30 minutes to swell the CTC resin. DCM was filtered and discharged. A separately prepared mixed solution of Fmoc-Asp(OH)-pip (50.07 mg, 0.119 mmol), DIPEA (58 μL, 0.331 mmol), MeTHF (1.2 mL) and DCM (1.2 mL) was added to the CTC resin and the mixture was shaken for 17 hours at room temperature. The reaction conversion ratio was 100%. After filtration, a DMF mixed solution (DMF:methanol: DIPEA=85:10:5 (total: 2.3 mL)) was added to the CTC resin and the mixture was shaken for 2 hours at room temperature. The CTC resin was washed four times with DMF (1.5 mL) and four times with methanol (1.5 mL), then the CTC resin was dried by vacuum pump to obtain Fmoc-Asp(O-CTC)-pip (190.9 mg). The yield by the Fmoc quantitation method was 96%.

Example 2-1-3: CTC Resin is Swollen with DCM and Loading Reaction is Performed in Mixed Solvent of MeTHF:DCM=1:2

1.36 mmol/g of CTC resin (147.62 mg, 0.201 mmol) was placed in a column for solid-phase synthesis, to which DCM (1.2 mL) was added and the mixture was shaken for 30 minutes to swell the CTC resin. DCM was filtered and discharged. A separately prepared mixed solution of Fmoc-Asp(OH)-pip (50.34 mg, 0.119 mmol), DIPEA (58 μL, 0.331 mmol), MeTHF (0.4 mL) and DCM (0.8 mL) was added to the CTC resin and the mixture was shaken for 6 hours at room temperature. The reaction conversion ratio was 100%. After filtration, a DMF mixed solution (DMF:methanol:DIPEA=85:10:5 (total: 2.3 mL)) was added to the CTC resin and the mixture was shaken for 2 hours at room temperature. After filtration, the CTC resin was washed four times with DMF (1.5 mL) and four times with methanol (1.5 mL), then the CTC resin was dried by vacuum pump to obtain Fmoc-Asp(O-CTC)-pip (184.7 mg). The yield by the Fmoc quantitation method was quantitative.

Example 2-2-1: CTC Resin is Swollen with DCM and Loading Reaction is Performed in Mixed Solvent of MTBE:DCM=1:1

1.36 mmol/g of CTC resin (148.84 mg, 0.202 mmol) was placed in a column for solid-phase synthesis, to which DCM (1.2 mL) was added and the mixture was shaken for 30 minutes to swell the CTC resin. DCM was filtered and discharged. A separately prepared mixed solution of Fmoc-Asp(OH)-pip (50.83 mg, 0.120 mmol), DIPEA (58 μL, 0.331 mmol), MTBE (0.6 mL) and DCM (0.6 mL) was added to the CTC resin and the mixture was shaken for 18 hours at room temperature. The reaction conversion ratio was 100%. After filtration, a DMF mixed solution (DMF:methanol:DIPEA=85:10:5 (total: 1.2 mL)) was added to the CTC resin and the mixture was shaken for 2 hours at room temperature. After filtration, the CTC resin was washed four times with DMF (1.5 mL) and four times with methanol (1.5 mL), then the CTC resin was dried by vacuum pump to obtain Fmoc-Asp(O-CTC)-pip (193.1 mg). The yield by the Fmoc quantitation method was 86%.

Example 2-2-2: CTC Resin is Swollen with DCM and Loading Reaction is Performed in Mixed Solvent of MTBE:DCM=1:2

1.36 mmol/g of CTC resin (147.61 mg, 0.201 mmol) was placed in a column for solid-phase synthesis, to which DCM (1.2 mL) was added and the mixture was shaken for 30 minutes to swell the CTC resin. DCM was filtered and discharged. A separately prepared mixed solution of Fmoc-Asp(OH)-pip (50.04 mg, 0.118 mmol), DIPEA (58 μL, 0.331 mmol), MTBE (0.4 mL) and DCM (0.8 mL) was added to the CTC resin and the mixture was shaken for 6 hours at room temperature. The reaction conversion ratio was 100%. After filtration, a DMF mixed solution (DMF:methanol:DIPEA=85:10:5 (total: 1.2 mL)) was added to the CTC resin and the mixture was shaken for 2 hours at room temperature. After filtration, the CTC resin was washed four times with DMF (1.5 mL) and four times with methanol (1.5 mL), then the CTC resin was dried by vacuum pump to obtain Fmoc-Asp(O-CTC)-pip (186.8 mg). The yield by the Fmoc quantitation method was 86%.

Example 2-3-1: CTC Resin is Swollen with DCM and Loading Reaction is Performed in Mixed Solvent of CPME:DCM=1:1

1.36 mmol/g of CTC resin (147.63 mg, 0.201 mmol) was placed in a column for solid-phase synthesis, to which DCM (1.2 mL) was added and the mixture was shaken for 30 minutes to swell the CTC resin. DCM was filtered and discharged. A separately prepared mixed solution of Fmoc-Asp(OH)-pip (50.12 mg, 0.119 mmol), DIPEA (58 μL, 0.331 mmol), CPME (0.6 mL) and DCM (0.6 mL) was added to the CTC resin and the mixture was shaken for 6 hours at room temperature. The reaction conversion ratio was 100%. After filtration, a DMF mixed solution (DMF:methanol:DIPEA=85:10:5 (total: 1.2 mL)) was added to the CTC resin and the mixture was shaken for 2 hours at room temperature. After filtration, the CTC resin was washed four times with DMF (1.5 mL) and four times with methanol (1.5 mL), then the CTC resin was dried by vacuum pump to obtain Fmoc-Asp(O-CTC)-pip (188.7 mg). The yield by the Fmoc quantitation method was 85%.

Example 2-3-2: CTC Resin is Swollen with DCM and Loading Reaction is Performed in Mixed Solvent of CPME:DCM=1:2

1.36 mmol/g of CTC resin (148.03 mg, 0.201 mmol) was placed in a column for solid-phase synthesis, to which DCM (1.2 mL) was added and the mixture was shaken for 30 minutes to swell the CTC resin. DCM was filtered and discharged. A separately prepared mixed solution of Fmoc-Asp(OH)-pip (50.28 mg, 0.119 mmol), DIPEA (58 μL, 0.331 mmol), CPME (0.4 mL) and DCM (0.8 mL) was added to the CTC resin and the mixture was shaken for 6 hours at room temperature. The reaction conversion ratio was 100%. After filtration, a DMF mixed solution (DMF:methanol:DIPEA=85:10:5 (total: 1.2 mL)) was added to the CTC resin and the mixture was shaken for 2 hours at room temperature. After filtration, the CTC resin was washed four times with DMF (1.5 mL) and four times with methanol (1.5 mL), then the CTC resin was dried by vacuum pump to obtain Fmoc-Asp(O-CTC)-pip (189.1 mg). The yield by the Fmoc quantitation method was 89%.

Example 2-3-2-2: Experiment from the Deprotection Reaction of Fmoc-Asp(O-tBu)-Pip Through the Loading Step. CTC Resin is Swollen With DCM and Loading Reaction is Performed in Mixed Solvent of CPME:DCM=1:2

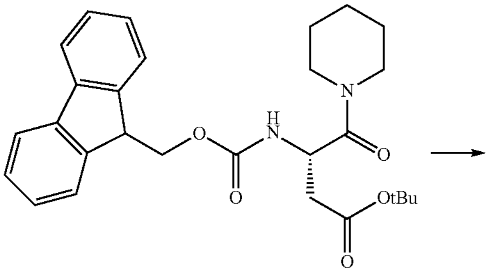

Fmoc-Asp(O—tBu)-pip

-continued

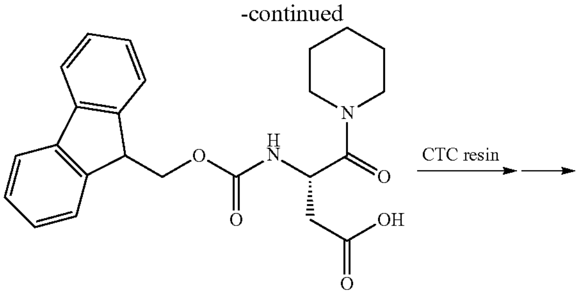

Fmoc-Asp(OH)-pip

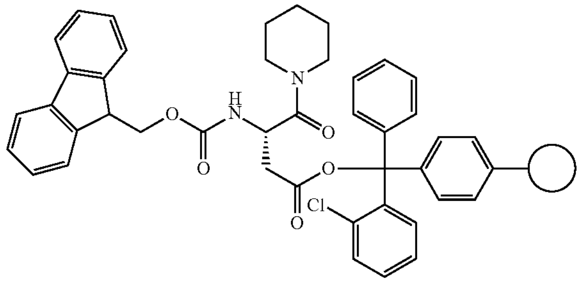

Fmoc-Asp(O-CTC)-pip

Fmoc-Asp(O-tBu)-pip (9.19 g, 19.2 mmol) was dissolved in MeTHF (46.0 mL). To the solution was added HMDS (4.8 mL, 23.0 mmol) at 0° C., then TMSOTf (3.8 mL, 21.2 mmol) was added dropwise. The reaction solution was heated to 25° C., then stirred for 1 hour. At 0° C., a 5% sodium carbonate solution (92 mL) was added to the reaction solution, which was heated to 25° C., and then stirred for 1 hour. After a back-extraction using MTBE (46 mL), the aqueous layer was washed with MTBE (92 mL). CPME (46 mL) was added to the aqueous layer, followed by phosphoric acid (4.6 mL, 96 mmol). After discharging the aqueous layer, the organic layer was washed with a 15% sodium chloride solution (40 mL) twice. $Na_2SO_4$ (6.84 g, 0.75 w/w) was added to the obtained CPME solution, which was then stirred for 30 minutes. $Na_2SO_4$ was removed by filtration and washed with CPME (20 mL). Of the 55.2828 g of CPME solution of Fmoc-Asp(OH)-pip obtained, 52.2534 g was used to proceed to the next step.

1.00 mmol/g of CTC resin (18.00 g, 18.00 mmol) was placed in a column for solid-phase synthesis, to which DCM (180 mL) was added and the mixture was shaken for 30 minutes to swell the CTC resin. After filtration, the CPME solution (48 mL) containing Fmoc-Asp(OH)-pip (6.08 g, 14.40 mmol) obtained above, DIPEA (7.02 mL, 40.0 mmol), and DCM (96 mL) were added to the CTC resin and the mixture was shaken for 23 hours at room temperature. The reaction conversion ratio was 98%. After filtration, a DMF mixed solution (DMF:methanol:DIPEA=85:10:5 (total: 144 mL)) was added to the CTC resin and the mixture was shaken for 2 hours at room temperature. After filtration, the CTC resin was washed four times with DMF (180 mL) and four times with methanol (180 mL), then the CTC resin was dried by vacuum pump to obtain Fmoc-Asp(O-CTC)-pip (25.0996 g). The yield by the Fmoc quantitation method was 92%. The obtained Fmoc-Asp(O-CTC)-pip (0.9993 g) was placed in a column for solid-phase synthesis, to which DMF (8 mL) was added, and then the column was shaken for 30 minutes. After filtration, washing was performed four times with DCM (8 mL). A 1% TFA/DCM solution (8 mL) was added and the mixture was shaken for 1 minute to cleave the amino acids from the resin. After filtration, the filtrate was set aside. A 1% TFA-DCM solution (8 mL) was added again to the resin, which was shaken for 1 minute, and the filtrate was collected after filtration (this operation was repeated four times). The resin was further washed with DCM (8 mL) twice. All the filtrates and the washing liquids were mixed and concentrated under reduced pressure. The concentrated residue was dried by vacuum pump to obtain 322 mg of Fmoc-Asp(OH)-pip. The yield by the isolation was 86%.

Example 2-4-1: CTC Resin is Swollen with DCM and Loading Reaction is Performed in DCM 1.36 mmol/g of CTC resin (144.9 mg, 0.200 mmol) was placed in a column for solid-phase synthesis, to which DCM (1.2 mL) was added and the mixture was shaken for 30 minutes to swell the CTC resin. After filtration, a DCM solution (2.3 mL) of Fmoc-Asp(OH)-pip (50.42 mg, 0.117 mmol) and DIPEA (58 μL, 0.331 mmol) was added to the CTC resin and the mixture was shaken for 3 hours at room temperature. The reaction conversion ratio was 100%. After filtration, a DMF mixed solution (DMF:methanol: DIPEA=85:10:5 (total: 1.2 mL)) was added to the CTC resin and the mixture was shaken for 2 hours at room temperature. After filtration, the CTC resin was washed four times with DMF (1.5 mL) and four times with methanol (1.5 mL), then the CTC resin was dried by vacuum pump to obtain Fmoc-Asp(O-CTC)-pip (183.7 mg). The yield by the Fmoc quantitation method was 94%.

Example 2-5-1: CTC Resin is Swollen with MeTHF and Loading Reaction is Performed in MeTHF 1.36 mmol/g of CTC resin (147.8 mg, 0.200 mmol) was placed in a column for solid-phase synthesis, to which MeTHF (1.2 mL) was added and the mixture was shaken for 30 minutes to swell the CTC resin. After filtration, a MeTHF solution (1.2 mL) of Fmoc-Asp(OH)-pip (49.94 mg, 0.117 mmol) and DIPEA (58 μL, 0.331 mmol) was added to the CTC resin and the mixture was shaken for 25 hours at room temperature. The reaction conversion ratio was 59%. After filtration, a DMF mixed solution (DMF:methanol: DIPEA=85:10:5 (total: 1.2 mL)) was added to the CTC resin and the mixture was shaken for 2 hours at room temperature. After filtration, the CTC resin was washed four times with DMF (1.5 mL) and four times with methanol (1.5 mL), then the CTC resin was dried by vacuum pump to obtain Fmoc-Asp(O-CTC)-pip (173.4 mg). The yield by the Fmoc quantitation method was 56%.

Example 3: Reaction of Loading Fmoc-MeAsp(OH)-pyrro on CTC Resin

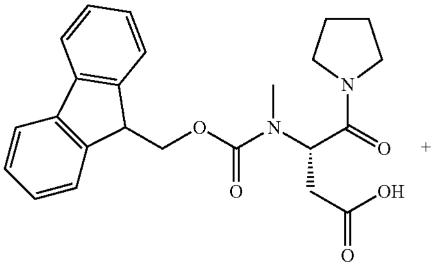

Fmoc-MeAsp(OH)-pyrro

-continued

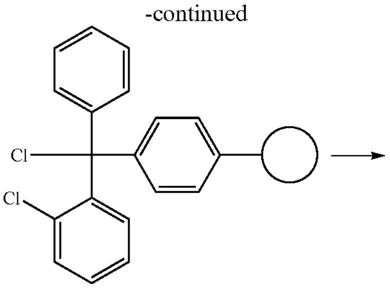

CTC resin

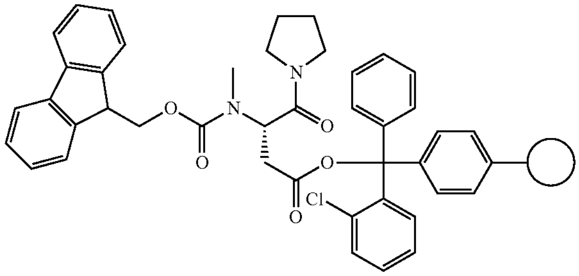

Fmoc-MeAsp(O-CTC)-pyrro

Example 3-1-1: CTC Resin is Swollen with DCM and Loading Reaction is Performed in Mixed Solvent of MeTHF:DCM=1:1

1.36 mmol/g of CTC resin (152.5 mg, 0.207 mmol) was placed in a column for solid-phase synthesis, to which DCM (1.5 mL) was added and the mixture was shaken for 30 minutes to swell the CTC resin. DCM was filtered and discharged. A separately prepared mixed solution of Fmoc-MeAsp(OH)-pyrro (50.53 mg, 0.120 mmol), DIPEA (60 μL, 0.343 mmol), MeTHF (0.6 mL) and DCM (0.6 mL) was added to the CTC resin and the mixture was shaken for 18 hours at room temperature. The reaction conversion ratio was 100%. After filtration, a DMF mixed solution (DMF:methanol:DIPEA=85:10:5 (total: 1.2 mL)) was added to the CTC resin and the mixture was shaken for 2 hours at room temperature. After filtration, the CTC resin was washed four times with DMF (1.5 mL) and four times with methanol (1.5 mL), then the CTC resin was dried by vacuum pump to obtain Fmoc-MeAsp(O-CTC)-pyrro (157.9 mg). The yield by the Fmoc quantitation method was 78%.

Example 3-1-2: CTC Resin is Swollen with DCM and Loading Reaction is Performed in Mixed Solvent of MeTHF:DCM=1:2

1.36 mmol/g of CTC resin (151.9 mg, 0.207 mmol) was placed in a column for solid-phase synthesis, to which DCM (1.5 mL) was added and the mixture was shaken for 30 minutes to swell the CTC resin. DCM was filtered and discharged. A separately prepared mixed solution of Fmoc-MeAsp(OH)-pyrro (50.58 mg, 0.120 mmol), DIPEA (60 μL, 0.343 mmol), MeTHF (0.4 mL) and DCM (0.8 mL) was added to the CTC resin and the mixture was shaken for 18 hours at room temperature. The reaction conversion ratio was 100%. After filtration, a DMF mixed solution (DMF:methanol:DIPEA=85:10:5 (total: 1.2 mL)) was added to the CTC resin and the mixture was shaken for 2 hours at room temperature. After filtration, the CTC resin was washed four times with DMF (1.5 mL) and four times with methanol (1.5 mL), then the CTC resin was dried by vacuum pump to obtain Fmoc-MeAsp(O-CTC)-pyrro (210.5 mg). The yield by the Fmoc quantitation method was 91%.

Example 3-2-1: CTC Resin is Swollen with DCM and Loading Reaction is Performed in Mixed Solvent of MTBE:DCM=1:1

1.36 mmol/g of CTC resin (152.5 mg, 0.207 mmol) was placed in a column for solid-phase synthesis, to which DCM (1.5 mL) was added and the mixture was shaken for 30 minutes to swell the CTC resin. DCM was filtered and discharged. A separately prepared mixed solution of Fmoc-MeAsp(OH)-pyrro (50.42 mg, 0.119 mmol), DIPEA (60 μL, 0.343 mmol), MTBE (0.6 mL) and DCM (0.6 mL) was added to the CTC resin and the mixture was shaken for 18 hours at room temperature. The reaction conversion ratio was 100%. After filtration, a DMF mixed solution (DMF:methanol:DIPEA=85:10:5 (total: 1.2 mL)) was added to the CTC resin and the mixture was shaken for 2 hours at room temperature. After filtration, the CTC resin was washed four times with DMF (1.5 mL) and four times with methanol (1.5 mL), then the CTC resin was dried by vacuum pump to obtain Fmoc-MeAsp(O-CTC)-pyrro (193.9 mg). The yield by the Fmoc quantitation method was 91%.

Example 3-2-2: CTC Resin is Swollen with DCM and Loading Reaction is Performed in Mixed Solvent of MTBE:DCM=1:2

1.36 mmol/g of CTC resin (152.1 mg, 0.207 mmol) was placed in a column for solid-phase synthesis, to which DCM (1.5 mL) was added and the mixture was shaken for 30 minutes to swell the CTC resin. DCM was filtered and discharged. A separately prepared mixed solution of Fmoc-MeAsp(OH)-pyrro (50.63 mg, 0.120 mmol), DIPEA (60 μL, 0.343 mmol), MTBE (0.4 mL) and DCM (0.8 mL) was added to the CTC resin and the mixture was shaken for 18 hours at room temperature. The reaction conversion ratio was 100%. After filtration, a DMF mixed solution (DMF:methanol:DIPEA=85:10:5 (total: 1.2 mL)) was added to the CTC resin and the mixture was shaken for 2 hours at room temperature. After filtration, the CTC resin was washed four times with DMF (1.5 mL) and four times with methanol (1.5 mL), then the CTC resin was dried by vacuum pump to obtain Fmoc-MeAsp(O-CTC)-pyrro (198.5 mg). The yield by the Fmoc quantitation method was 87%.

Example 3-3-1: CTC Resin is Swollen with DCM and Loading Reaction is Performed in Mixed Solvent of CPME:DCM=1:1

1.36 mmol/g of CTC resin (152.4 mg, 0.207 mmol) was placed in a column for solid-phase synthesis, to which DCM (1.5 mL) was added and the mixture was shaken for 30 minutes to swell the CTC resin. DCM was filtered and discharged. A separately prepared mixed solution of Fmoc-MeAsp(OH)-pyrro (50.61 mg, 0.120 mmol), DIPEA (60 μL, 0.343 mmol), CPME (0.6 mL) and DCM (0.6 mL) was added to the CTC resin and the mixture was shaken for 18 hours at room temperature. The reaction conversion ratio was 100%. After filtration, a DMF mixed solution (DMF:methanol:DIPEA=85:10:5 (total: 1.2 mL)) was added to the CTC resin and the mixture was shaken for 2 hours at room temperature. After filtration, the CTC resin was washed four times with DMF (1.5 mL) and four times with methanol (1.5 mL), then the CTC resin was dried by vacuum pump to obtain Fmoc-MeAsp(O-CTC)-pyrro (158.0 mg). The yield by the Fmoc quantitation method was 70%.

Example 3-3-2: CTC Resin is Swollen with DCM and Loading Reaction is Performed in Mixed Solvent of CPME:DCM=1:2

1.36 mmol/g of CTC resin (152.6 mg, 0.207 mmol) was placed in a column for solid-phase synthesis, to which DCM (1.5 mL) was added and the mixture was shaken for 30 minutes to swell the CTC resin. DCM was filtered and discharged. A separately prepared mixed solution of Fmoc-MeAsp(OH)-pyrro (50.51 mg, 0.120 mmol), DIPEA (60 μL, 0.343 mmol), CPME (0.4 mL) and DCM (0.8 mL) was added to the CTC resin and the mixture was shaken for 18 hours at room temperature. The reaction conversion ratio was 100%. After filtration, a DMF mixed solution (DMF:methanol:DIPEA=85:10:5 (total: 1.2 mL)) was added to the CTC resin and the mixture was shaken for 2 hours at room temperature. After filtration, the CTC resin was washed four times with DMF (1.5 mL) and four times with methanol (1.5 mL), then the CTC resin was dried by vacuum pump to obtain Fmoc-MeAsp(O-CTC)-pyrro (196.4 mg). The yield by the Fmoc quantitation method was 85%.

Example 4: Reaction of Loading Fmoc-MeAsp(OH)—NMe2 on CTC Resin

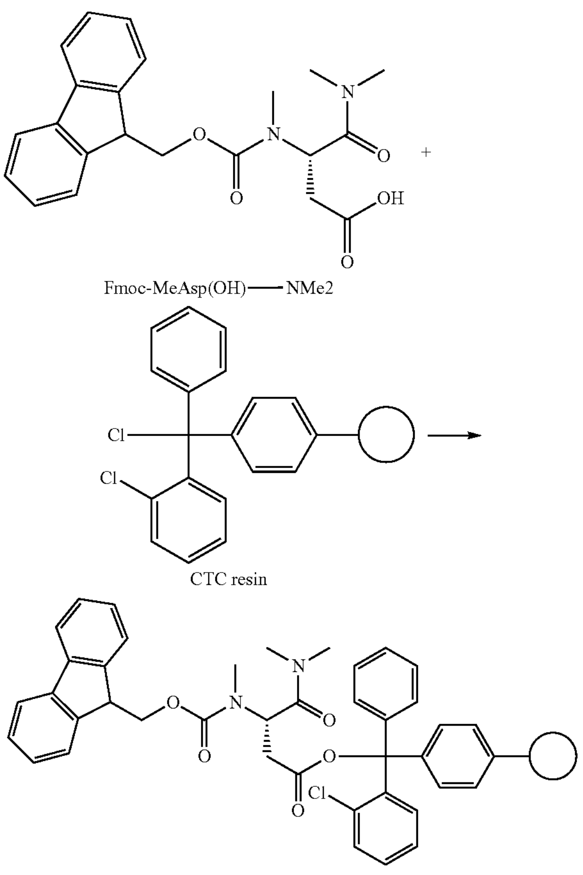
Fmoc-MeAsp(OH)—NMe2
CTC resin
Fmoc-MeAsp(O-CTC)-NMe2

Example 4-1-1: CTC Resin is Swollen with DCM and Loading Reaction is Performed in Mixed Solvent of MeTHF:DCM=1:1

1.36 mmol/g of CTC resin (164.02 mg, 0.223 mmol) was placed in a column for solid-phase synthesis, to which DCM (1.3 mL) was added and the mixture was shaken for 30 minutes to swell the CTC resin. After filtration, an amino acid solution of Fmoc-MeAsp(OH)—NMe2 (50.84 mg, 0.133 mmol) dissolved in a mixed solvent of MeTHF (0.65 mL) and DCM (0.65 mL), to which DIPEA (64 μL, 0.366 mmol) was added, was added to the CTC resin and the mixture was shaken for 16 hours at room temperature. The reaction conversion ratio was 100%. After filtration, a DMF mixed solution (DMF:methanol:DIPEA=85:10:5 (total: 1.3 mL)) was added to the CTC resin and the mixture was shaken for 2 hours at room temperature. After filtration, the CTC resin was washed four times with DMF (1.6 mL) and four times with methanol (1.6 mL), then the CTC resin was dried by vacuum pump to obtain Fmoc-MeAsp(O-CTC)—NMe2 (205.0 mg). The yield by the Fmoc quantitation method was 94%.

Example 4-1-2: CTC Resin is Swollen with DCM and Loading Reaction is Performed in Mixed Solvent of MeTHF:DCM=1:2

1.36 mmol/g of CTC resin (163.54 mg, 0.222 mmol) was placed in a column for solid-phase synthesis, to which DCM (1.3 mL) was added and the mixture was shaken for 30 minutes to swell the CTC resin. After filtration, an amino acid solution of Fmoc-MeAsp(OH)—NMe2 (50.17 mg, 0.132 mmol) dissolved in MeTHF (0.44 mL) and DCM (0.88 mL), to which DIPEA (58 μL, 0.331 mmol) was added, was added to the CTC resin and the mixture was shaken for 18 hours at room temperature. The reaction conversion ratio was 100%. After filtration, a DMF mixed solution (DMF:methanol:DIPEA=85:10:5 (total: 1.3 mL)) was added to the CTC resin and the mixture was shaken for 2 hours at room temperature. After filtration, the CTC resin was washed four times with DMF (1.6 mL) and four times with methanol (1.6 mL), then the CTC resin was dried by vacuum pump to obtain Fmoc-MeAsp(O-CTC)—NMe2 (213.5 mg). The yield by the Fmoc quantitation method was 82%.

Example 4-2-1: CTC Resin is Swollen with DCM and Loading Reaction is Performed in Mixed SOLVENT of MTBE:DCM=1:1

1.36 mmol/g of CTC resin (163.09 mg, 0.221 mmol) was placed in a column for solid-phase synthesis, to which DCM (1.3 mL) was added and the mixture was shaken for 30 minutes to swell the CTC resin. After filtration, an amino acid solution in which Fmoc-MeAsp(OH)—NMe2 (50.49 mg, 0.132 mmol) was dissolved in a mixed solvent of MTBE (0.65 mL) and DCM (0.65 mL), then DIPEA (64 μL, 0.366 mmol) was added, was added to the CTC resin and the mixture was shaken for 16 hours at room temperature. The reaction conversion ratio was 100%. After filtration, a DMF mixed solution (DMF:methanol:DIPEA=85:10:5 (total: 2.3 mL)) was added to the CTC resin and the mixture was shaken for 2 hours at room temperature. After filtration, the CTC resin was washed four times with DMF (1.6 mL) and four times with methanol (1.6 mL), then the CTC resin was dried by vacuum pump to obtain Fmoc-MeAsp(O-CTC)—NMe2 (207.3 mg). The yield by the Fmoc quantitation method was 89%.

Example 4-2-2: CTC Resin is Swollen with DCM and Loading Reaction is Performed in Mixed Solvent of MTBE:DCM=1:2

1.36 mmol/g of CTC resin (163.51 mg, 0.222 mmol) was placed in a column for solid-phase synthesis, to which DCM (1.3 mL) was added and the mixture was shaken for 30 minutes to swell the CTC resin. After filtration, an amino acid solution in which Fmoc-MeAsp(OH)—NMe2 (50.71 mg, 0.128 mmol) was dissolved in MTBE (0.4 mL) and DCM (0.8 mL), then DIPEA (58 μL, 0.331 mmol) was added, was added to the CTC resin and the mixture was shaken for 18 hours at room temperature. The reaction conversion ratio was 100%. After filtration, a DMF mixed solution (DMF:methanol:DIPEA=85:10:5 (total: 1.3 mL)) was added to the CTC resin and the mixture was shaken for 2 hours at room temperature. After filtration, the CTC resin was washed four times with DMF (1.6 mL) and four times with methanol (1.6 mL), then the CTC resin was dried by vacuum pump to obtain Fmoc-MeAsp(O-CTC)—NMe2 (209.7 mg). The yield by the Fmoc quantitation method was 95%.

Example 4-3-1: CTC Resin is Swollen with DCM and Loading Reaction is Performed in Mixed Solvent of CPME:DCM=1:1

1.36 mmol/g of CTC resin (162.71 mg, 0.221 mmol) was placed in a column for solid-phase synthesis, to which DCM (1.3 mL) was added and the mixture was shaken for 30 minutes to swell the CTC resin. After filtration, an amino acid solution in which Fmoc-MeAsp(OH)—NMe2 (49.84 mg, 0.130 mmol) was dissolved in CPME (0.65 mL) and DCM (0.65 mL), then DIPEA (64 μL, 0.366 mmol) was added, was added to the CTC resin and the mixture was shaken for 18 hours at room temperature. The reaction conversion ratio was 100%. After filtration, a DMF mixed solution (DMF:methanol:DIPEA=85:10:5 (total: 1.3 mL)) was added to the CTC resin and the mixture was shaken for 2 hours at room temperature. After filtration, the CTC resin was washed four times with DMF (1.6 mL) and four times with methanol (1.6 mL), then the CTC resin was dried by vacuum pump to obtain Fmoc-MeAsp(O-CTC)—NMe2 (204.1 mg). The yield by the Fmoc quantitation method was 85%.

Example 4-3-2: CTC Resin is Swollen with DCM and Loading Reaction is Performed in Mixed Solvent of CPME:DCM=1:2

1.36 mmol/g of CTC resin (163.32 mg, 0.222 mmol) was placed in a column for solid-phase synthesis, to which DCM (1.3 mL) was added and the mixture was shaken for 30 minutes to swell the CTC resin. After filtration, an amino acid solution in which Fmoc-MeAsp(OH)—NMe2 (50.19 mg, 0.131 mmol) was dissolved in a mixed solvent of CPME (0.44 mL) and DCM (0.88 mL), then DIPEA (62 μL, 0.3 mmol) was added, was added to the CTC resin and the mixture was shaken for 18 hours at room temperature. The reaction conversion ratio was 100%. After filtration, a DMF mixed solution (DMF:methanol:DIPEA=85:10:5 (total: 1.3 mL)) was added to the CTC resin and the mixture was shaken for 2 hours at room temperature. After filtration, the CTC resin was washed four times with DMF (1.6 mL) and four times with methanol (1.6 mL), then the CTC resin was dried by vacuum pump to obtain Fmoc-MeAsp(O-CTC)—NMe2 (214.3 mg). The yield by the Fmoc quantitation method was 89%.

INDUSTRIAL APPLICABILITY

The present invention is useful for the production of a peptide compound containing at least one N-substituted amino acid, using a solid-phase method.

The invention claimed is:

1. A method for producing a peptide compound comprising at least one N-substituted amino acid, a salt thereof, or a solvate thereof, the method comprising a step of bringing a resin for solid-phase synthesis swollen in a solvent comprising a first solvent into contact with (i) a solution comprising an amino acid and a second solvent, or (ii) a solution comprising an amino acid, a second solvent, and a third solvent, to obtain an amino acid loaded on the resin for solid-phase synthesis (Step 1), wherein the first solvent and the third solvent are each independently selected from halogenated solvents, the second solvent is an ether solvent, the amino acid is a non-natural amino acid having an amino group, and the non-natural amino acid is loaded on the resin for solid-phase synthesis by a carboxyl group bound to a carbon atom at a β-position or a carbon atom at a γ-position of the amino group.

2. A method for producing an amino acid loaded on a resin for solid-phase synthesis, the method comprising a step of bringing a resin for solid-phase synthesis swollen in a solvent comprising a first solvent into contact with (i) a solution comprising an amino acid and a second solvent, or (ii) a solution comprising an amino acid, a second solvent, and a third solvent, wherein the first solvent and the third solvent are each independently selected from halogenated solvents, the second solvent is an ether solvent, the amino acid is a non-natural amino acid having an amino group, and the non-natural amino acid is loaded on the resin for solid-phase synthesis by a carboxyl group bound to a carbon atom at a β-position or a carbon atom at a γ-position of the amino group.

3. The method according to claim 1, wherein the step of bringing comprises bringing the resin into contact with the solution comprising the amino acid and the second solvent.

4. The method according to claim 1, wherein the step of bringing comprises bringing the resin into contact with the solution comprising the amino acid, the second solvent, and the third solvent.

5. The method according to claim 1, wherein the first solvent and the third solvent are the same solvent.

6. The method according to claim 1, wherein the volume ratio of the second solvent to the third solvent is 1:1 to 1:10.

7. The method according to claim 1, wherein the solution comprising the amino acid and the second solvent is a solution obtained by an extraction operation comprising the use of the second solvent, which is performed after a deprotection reaction of a protective group for the amino acid's carboxyl group prior to Step 1, and a subsequent optional dehydration operation.

8. The method according to claim 1, wherein the solution comprising the amino acid, the second solvent, and the third solvent is a solution obtained by adding the third solvent to a solution obtained by an extraction operation comprising the use of the second solvent, which is performed after a deprotection reaction of a protective group for the amino acid's carboxyl group prior to Step 1, and a subsequent optional dehydration operation.

9. The method according to claim 7, wherein the dehydration operation is performed with a desiccant.

10. The method according to claim 7, wherein the protective group for the carboxyl group can be removed with an acid.

11. The method according to claim 1, wherein the resin for solid-phase synthesis is a CTC resin, a Wang resin, a SASRIN resin, a Trt resin, an Mtt resin, or an Mmt resin.

12. The method according to claim 1, wherein the peptide compound comprises two or more N-substituted amino acids.

13. A method for producing a cyclic peptide compound, a salt thereof, or a solvate thereof, comprising the following steps:

a step of obtaining a peptide compound comprising at least one N-substituted amino acid, a salt thereof, or a solvate thereof, according to the method according to claim 1, a step of removing the resin for solid-phase synthesis, and a step of cyclizing a C-terminus group and an N-terminus group of the peptide compound, the salt thereof, or the solvate thereof to form a cyclic portion.

14. The method according to claim 1, wherein the first solvent is selected from the group consisting of DCM, DCE, chloroform, chlorobenzene, and carbon tetrachloride.

15. The method according to claim 1, wherein the second solvent is selected from the group consisting of MeTHF, MTBE, CPME, THE, IPE, DME, diethyl ether, and dioxane.

16. The method according to claim 1, wherein the third solvent is selected from the group consisting of DCM, DCE, chloroform, chlorobenzene, and carbon tetrachloride.

17. The method according to claim 1, wherein the non-natural amino acid is a non-natural N-substituted amino acid.

18. The method according to claim 1, wherein the non-natural amino acid comprises an aminocarbonyl group.

19. The method according to claim 1, wherein the non-natural amino acid loaded on the resin for solid-phase synthesis by a carboxyl group bound to a carbon atom at a β-position or a carbon atom at a γ-position of the amino group is aminocarbonylated aspartic acid, aminocarbonylated glutamic acid, 2-aminobutanoic acid, or an N-substituted form thereof, and wherein the aminocarbonylated aspartic acid is aminocarbonylated at a free carboxyl group of aspartic acid and the aminocarbonylated glutamic acid is aminocarbonylated at a free carboxyl group of glutamic acid.

20. The method according to claim 1, wherein 30% or more of the total number of amino acids constituting the peptide compound are N-substituted amino acids.

* * * * *